US 9,552,899 B2

(12) United States Patent
Specht et al.

(10) Patent No.: US 9,552,899 B2
(45) Date of Patent: Jan. 24, 2017

(54) CERAMIC BUSHING FOR AN IMPLANTABLE MEDICAL DEVICE

(71) Applicant: Heraeus Precious Metals GmbH & Co. KG, Hanau (DE)

(72) Inventors: Heiko Specht, Hanau (DE); Jeremy Glynn, Buffalo, MN (US)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 0 days.

(21) Appl. No.: 14/729,560

(22) Filed: Jun. 3, 2015

(65) Prior Publication Data
US 2015/0270025 A1    Sep. 24, 2015

Related U.S. Application Data

(63) Continuation of application No. 13/361,322, filed on Jan. 30, 2012, now abandoned.
(Continued)

(30) Foreign Application Priority Data

Jan. 31, 2011  (DE) .................. 10 2011 009 867

(51) Int. Cl.
*H01B 1/02* (2006.01)
*A61N 1/02* (2006.01)
(Continued)

(52) U.S. Cl.
CPC ...... *H01B 1/02* (2013.01); *A61N 1/02* (2013.01); *A61N 1/3754* (2013.01); *H01B 1/023* (2013.01);
(Continued)

(58) Field of Classification Search
CPC .......... A61N 1/05; A61N 1/36; A61N 1/3752; A61N 1/3754; A61N 1/375; A61N 1/3756; A61F 2/02; H01B 17/30; H01B 17/303; H01B 17/305; H01B 17/306; H01B 1/02; H01B 1/023; H01G 4/35; H01M 2/065; H01M 2/08; C04B 35/111; C04B 35/117; H02G 15/013
(Continued)

(56) References Cited

U.S. PATENT DOCUMENTS 3,025,441 A    3/1962  West
3,063,144 A    11/1962 Palmour, III
(Continued)

FOREIGN PATENT DOCUMENTS

CN    1452232    10/2003
DE    69729719    7/2005
(Continued)

OTHER PUBLICATIONS

The Final Office Action for U.S. Appl. No. 13/361,322 mailed Aug. 24, 2015 (21 pages).
(Continued)

*Primary Examiner* — Dimary Lopez Cruz
(74) *Attorney, Agent, or Firm* — Dicke, Billig & Czaja, PLLC

(57) ABSTRACT

An electrical bushing for use in a housing of an implantable medical device is proposed. The electrical bushing includes at least one electrically insulating base body and at least one electrical conducting element. The conducting element establishes, through the base body, at least one electrically conductive connection between an internal space of the housing and an external space. The conducting element is hermetically sealed with respect to the base body, at least in part. The at least one conducting element includes at least
(Continued)

one cermet. The cermet of the conducting element and the base body include one or more of the same ceramic compound.

14 Claims, 3 Drawing Sheets

Related U.S. Application Data

(60) Provisional application No. 61/438,000, filed on Jan. 31, 2011.

(51) Int. Cl.
  *H02G 15/013* (2006.01)
  *A61N 1/375* (2006.01)

(52) U.S. Cl.
  CPC ......... *H02G 15/013* (2013.01); *H04R 2225/67* (2013.01); *Y10T 29/49169* (2015.01); *Y10T 29/49206* (2015.01)

(58) Field of Classification Search
  USPC ... 174/11 BH, 14 BH, 17 R, 18, 50.5, 50.52, 174/50.53, 650, 152 GM, 520; 439/909; 607/4, 607/5, 36, 37, 116, 2; 429/181; 361/302, 307; 333/182
  See application file for complete search history.

(56) References Cited

U.S. PATENT DOCUMENTS

| | | |
|---|---|---|
| 3,646,405 A | 2/1972 | Wallis et al. |
| 3,979,187 A | 9/1976 | Scherer |
| 4,152,540 A | 5/1979 | Duncan et al. |
| 4,159,075 A | 6/1979 | Ljung et al. |
| 4,217,137 A | 8/1980 | Kraska et al. |
| 4,225,262 A | 9/1980 | Koop et al. |
| 4,315,054 A | 2/1982 | Sack et al. |
| 4,354,964 A | 10/1982 | Hing et al. |
| 4,488,673 A | 12/1984 | Hopper, Jr. |
| 4,602,956 A | 7/1986 | Partlow et al. |
| 4,678,868 A | 7/1987 | Kraska et al. |
| 4,991,582 A | 2/1991 | Byers et al. |
| 5,043,535 A | 8/1991 | Lin |
| 5,515,604 A | 5/1996 | Horine et al. |
| 5,601,638 A † | 2/1997 | Fukuda |
| 5,735,884 A | 4/1998 | Thompson et al. |
| 5,738,270 A | 4/1998 | Malmgren |
| 5,769,874 A | 6/1998 | Dahlberg |
| 5,796,019 A | 8/1998 | Lupton et al. |
| 5,861,714 A | 1/1999 | Wei et al. |
| 5,870,272 A | 2/1999 | Seifried et al. |
| 6,093,476 A | 7/2000 | Horiuchi et al. |
| 6,414,835 B1 | 7/2002 | Wolf et al. |
| 6,643,903 B2 | 11/2003 | Stevenson et al. |
| 6,660,116 B2 | 12/2003 | Wolf et al. |
| 6,841,731 B1 | 1/2005 | Zanello |
| 6,999,818 B2 | 2/2006 | Stevenson et al. |
| 7,035,076 B1 | 4/2006 | Stevenson |
| 7,038,900 B2 | 5/2006 | Stevenson et al. |
| 7,136,273 B2 | 11/2006 | Stevenson et al. |
| 7,145,076 B2 | 12/2006 | Knappen et al. |
| 7,174,219 B2 | 2/2007 | Wahlstrand et al. |
| 7,174,223 B2 | 2/2007 | Dalton et al. |
| 7,211,103 B2 † | 5/2007 | Greenberg |
| 7,260,434 B1 | 8/2007 | Lim et al. |
| 7,274,963 B2 | 9/2007 | Spadgenske |
| 7,341,802 B1 | 3/2008 | Ota et al. |
| 7,437,817 B2 | 10/2008 | Zhang et al. |
| 7,480,988 B2 | 1/2009 | Ok et al. |
| 7,502,217 B2 | 3/2009 | Zhao et al. |
| 7,561,917 B2 | 7/2009 | Wegrzyn, III et al. |
| 7,564,674 B2 | 7/2009 | Frysz et al. |
| 7,630,768 B1 | 12/2009 | Coffed et al. |
| 7,706,124 B2 | 4/2010 | Zhao et al. |
| 7,720,538 B2 | 5/2010 | Janzig et al. |
| 7,736,191 B1 | 6/2010 | Sochor |
| 7,742,817 B2 | 6/2010 | Malinowski et al. |
| 7,747,321 B2 | 6/2010 | Fischbach et al. |
| 7,761,165 B1 | 7/2010 | He et al. |
| 7,765,005 B2 | 7/2010 | Stevenson |
| 7,794,256 B1 | 9/2010 | Sochor |
| 7,901,761 B1 | 3/2011 | Jiang et al. |
| 7,930,032 B2 | 4/2011 | Teske et al. |
| 7,970,474 B2 | 6/2011 | Starke |
| 7,989,080 B2 | 8/2011 | Greenberg et al. |
| 8,000,804 B1 † | 8/2011 | Wessendorf |
| 8,065,009 B2 | 11/2011 | Biggs |
| 8,131,369 B2 | 3/2012 | Taylor et al. |
| 8,131,376 B1 | 3/2012 | Faraji et al. |
| 8,163,397 B2 | 4/2012 | Ok et al. |
| 8,179,658 B2 | 5/2012 | Brendel et al. |
| 8,288,654 B2 | 10/2012 | Taylor et al. |
| 8,289,105 B2 | 10/2012 | Chereson et al. |
| 8,326,425 B2 | 12/2012 | Sprain et al. |
| 8,346,362 B2 | 1/2013 | Kinney et al. |
| 8,355,785 B1 | 1/2013 | Hammond et al. |
| 8,378,239 B2 | 2/2013 | Lakner et al. |
| 8,391,983 B2 | 3/2013 | Lim |
| 8,494,635 B2 | 7/2013 | Troetzschel et al. |
| 8,497,435 B2 | 7/2013 | Nagata et al. |
| 8,528,201 B2 | 9/2013 | Troetzschel et al. |
| 8,538,530 B1 | 9/2013 | Orinski |
| 8,552,311 B2 | 10/2013 | Koester et al. |
| 8,626,310 B2 | 1/2014 | Barror et al. |
| 8,656,736 B2 | 2/2014 | Terao |
| 8,659,870 B2 | 2/2014 | Brendel et al. |
| 8,742,268 B2 | 6/2014 | Reisinger et al. |
| 8,825,162 B2 | 9/2014 | Reisinger |
| 8,894,914 B2 | 11/2014 | Pavlovic |
| 9,032,614 B2 | 5/2015 | Specht |
| 9,040,819 B2 | 5/2015 | Kempf et al. |
| 9,048,608 B2 | 6/2015 | Pavlovic |
| 9,088,093 B2 | 7/2015 | Reisinger et al. |
| 9,126,053 B2 | 9/2015 | Kempf et al. |
| 9,306,318 B2 | 4/2016 | Reisinger |
| 2001/0013756 A1 | 8/2001 | Mori et al. |
| 2004/0116976 A1 | 6/2004 | Spadgenske |
| 2004/0128016 A1 | 7/2004 | Stewart |
| 2006/0247714 A1 | 11/2006 | Taylor et al. |
| 2006/0259093 A1 | 11/2006 | Stevenson et al. |
| 2007/0183118 A1 | 8/2007 | Fu et al. |
| 2008/0060834 A1 | 3/2008 | Eck et al. |
| 2008/0060844 A1 | 3/2008 | Teske et al. |
| 2008/0119906 A1 | 5/2008 | Starke |
| 2008/0203917 A1 | 8/2008 | Maya |
| 2008/0269831 A1 | 10/2008 | Erickson |
| 2008/0314502 A1 † | 12/2008 | Ok |
| 2009/0192578 A1 | 7/2009 | Biggs |
| 2009/0281586 A1 | 11/2009 | Lim |
| 2010/0023086 A1 | 1/2010 | Lim |
| 2010/0109966 A1 | 5/2010 | Mateychuk et al. |
| 2010/0258342 A1 | 10/2010 | Parker |
| 2011/0034965 A1 | 2/2011 | Troetzschel et al. |
| 2011/0034966 A1 | 2/2011 | Troetzschel et al. |
| 2011/0048770 A1 | 3/2011 | Reiterer et al. |
| 2011/0186349 A1 | 8/2011 | Troetzschel et al. |
| 2012/0127627 A1 | 5/2012 | Brendel et al. |
| 2012/0193117 A1 | 8/2012 | Specht et al. |
| 2012/0193118 A1 | 8/2012 | Kempf et al. |
| 2012/0193119 A1 | 8/2012 | Kempf et al. |
| 2012/0193125 A1 | 8/2012 | Pavlovic et al. |
| 2012/0193141 A1 | 8/2012 | Reisinger et al. |
| 2012/0194981 A1 | 8/2012 | Kempf et al. |
| 2012/0197326 A1 | 8/2012 | Pavlovic |
| 2012/0197327 A1 | 8/2012 | Specht |
| 2012/0197335 A1 | 8/2012 | Reisinger |
| 2012/0197368 A1 | 8/2012 | Reisinger |
| 2012/0200011 A1 | 8/2012 | Pavlovic |
| 2012/0203294 A1 | 8/2012 | Troetzschel |
| 2014/0262494 A1 | 9/2014 | Reisinger et al. |

(56) References Cited

U.S. PATENT DOCUMENTS

| | | | |
|---|---|---|---|
| 2014/0368298 A1 | 12/2014 | Reisinger | |
| 2015/0122875 A1 | 5/2015 | Pavlovic et al. | |

FOREIGN PATENT DOCUMENTS

| | | |
|---|---|---|
| DE | 102006054249 | 5/2008 |
| DE | 102008021064 | 10/2009 |
| DE | 102009035971 | 2/2011 |
| DE | 102009035972 | 4/2011 |
| DE | 102010006837 | 8/2011 |
| DE | 102010006838 | 8/2011 |
| DE | 102010006689 | 9/2011 |
| DE | 102010006690 | 9/2011 |
| EP | 0877400 | 11/1998 |
| EP | 1685874 | 8/2006 |
| EP | 1754511 | 2/2007 |
| WO | 03073450 | 9/2003 |
| WO | 2004110555 | 12/2004 |
| WO | 2008103166 | 8/2008 |
| WO | 2010091435 | 8/2010 |

OTHER PUBLICATIONS

The Advisory Action for U.S. Appl. No. 13/361,340 mailed Feb. 22, 2016 (4 pages).
The Notice of Allowance for U.S. Appl. No. 13/361,374 mailed Dec. 3, 2015 (21 pages).
The Corrected Notice of Allowability for U.S. Appl. No. 13/361,374 mailed Feb. 11, 2016 (7 pages).
The Final Office Action for U.S. Appl. No. 13/361,388 mailed Sep. 11, 2015 (28 pages).
The Office Action for U.S. Appl. No. 14/474,569 mailed Mar. 21, 2016 (33 pages).
The Office Action for U.S. Appl. No. 14/593,637 mailed May 26, 2016 (37 pages).
The Restriction Requirement for U.S. Appl. No. 13/361,322 mailed Nov. 14, 2013 (7 pages).
The Office Action for U.S. Appl. No. 13/361,322 mailed Feb. 19, 2014 (26 pages).
The Final Office Action for U.S. Appl. No. 13/361,322 mailed Sep. 9, 2014 (17 pages).
The Office Action for U.S. Appl. No. 13/361,322 mailed Feb. 4, 2015 (19 pages).
The Office Action for U.S. Appl. No. 13/361,340 mailed Oct. 25, 2013 (20 pages).
The Office Action for U.S. Appl. No. 13/361,340 mailed Apr. 29, 2014 (18 pages).
The Final Office Action for U.S. Appl. No. 13/361,340 mailed Oct. 30, 2014 (21 pages).
The Office Action for U.S. Appl. No. 13/361,340 mailed Mar. 12, 2015 (23 pages).
The Restriction Requirement for U.S. Appl. No. 13/361,348 mailed Nov. 14, 2013 (7 pages).
The Office Action for U.S. Appl. No. 13/361,348 mailed Feb. 19, 2014 (23 pages).
The Final Office Action for U.S. Appl. No. 13/361,348 mailed Sep. 9, 2014 (19 pages).
The Notice of Allowance for U.S. Appl. No. 13/361,348 mailed Jan. 22, 2015 (9 pages).
The Office Action for U.S. Appl. No. 13/361,355 mailed date Aug. 7, 2013 (21 pages).
The Notice of Allowance for U.S. Appl. No. 13/361,355 mailed Jan. 16, 2014 (18 pages).
The Notice of Allowance for U.S. Appl. No. 14/293,596 mailed Mar. 17, 2015 (28 pages).
The Restriction Requirement for U.S. Appl. No. 13/361,362 mailed Nov. 14, 2013 (7 pages).
The Office Action for U.S. Appl. No. 13/361,362 mailed Feb. 19, 2014 (19 pages).
The Final Office Action for U.S. Appl. No. 13/361,362 mailed Sep. 9, 2014 (19 pages).
The Office Action for U.S. Appl. No. 13/361,370 mailed Oct. 29, 2013 (26 pages).
The Office Action for U.S. Appl. No. 13/361,370 mailed May 14, 2014 (18 pages).
The Final Office Action for U.S. Appl. No. 13/361,370 mailed Nov. 5, 2014 (19 pages).
The Notice of Allowance for U.S. Appl. No. 13/361,370 mailed May 1, 2015 (17 pages).
The Restriction Requirement for U.S. Appl. No. 13/361,374 mailed Mar. 5, 2013 (6 pages).
The Office Action for U.S. Appl. No. 13/361,374 mailed Oct. 4, 2013 (22 pages).
The Office Action for U.S. Appl. No. 13/361,374 mailed May 1, 2014 (20 pages).
The Final Office Action for U.S. Appl. No. 13/361,374 mailed Nov. 10, 2014 (19 pages).
The Office Action for U.S. Appl. No. 13/361,374 mailed May 18, 2015 (12 pages).
The Restriction Requirement for U.S. Appl. No. 13/361,383 mailed Feb. 27, 2013 (6 pages).
The Office Action for U.S. Appl. No. 13/361,383 mailed Nov. 13, 2013 (22 pages).
The Notice of Allowance for U.S. Appl. No. 13/361,383 mailed Apr. 25, 2014 (18 pages).
The Office Action for U.S. Appl. No. 13/361,388 mailed Feb. 11, 2014 (24 pages).
The Final Office Action for U.S. Appl. No. 13/361,388 mailed Jul. 31, 2014 (32 pages).
The Office Action for U.S. Appl. No. 13/361,388 mailed Feb. 9, 2015 (29 pages).
Hussain, et al., "Electrical conductivity of an insulator matrix (alumina) and conductor particle (molybdenum) composites", Journal of the European Ceramic Society, vol. 23, Issue 2, Feb. 2003, pp. 315-321.
The Office Action for U.S. Appl. No. 13/361,398 mailed Mar. 7, 2014 (26 pages).
The Notice of Allowance for U.S. Appl. No. 13/361,398 mailed Jul. 25, 2014 (11 pages).
The Restriction Requirement for U.S. Appl. No. 13/361,404 mailed Apr. 8, 2013 (6 pages).
The Restriction Requirement for U.S. Appl. No. 13/361,404 mailed Oct. 9, 2013 (5 pages).
The Office Action for U.S. Appl. No. 13/361,404 mailed Feb. 27, 2014 (19 pages).
The Final Office Action for U.S. Appl. No. 13/361,404 mailed Oct. 9, 2014 (12 pages).
The Notice of Allowance for U.S. Appl. No. 13/361,404 mailed Jan. 28, 2015 (6 pages).
The Restriction Requirement for U.S. Appl. No. 13/361,411 mailed Mar. 10, 2014 (7 pages).
The Office Action for U.S. Appl. No. 13/361,411 mailed Aug. 1, 2014 (18 pages).
The Notice of Allowance for U.S. Appl. No. 13/361,411 mailed Jan. 20, 2015 (8 pages).

† cited by third party

CERAMIC BUSHING FOR AN IMPLANTABLE MEDICAL DEVICE

CROSS-REFERENCE TO RELATED APPLICATIONS

This application is a continuation of U.S. patent application Ser. No. 13/361,322, entitled "CERAMIC BUSHING FOR AN IMPLANTABLE MEDICAL DEVICE," having a filing date of Jan. 30, 2012, which claims the benefit of the filing date of U.S. Provisional Patent Application Ser. No. 61/438,000, filed Jan. 31, 2011, entitled "CERAMIC BUSHING FOR AN IMPLANTABLE MEDICAL DEVICE," which claims priority to German Patent Application No. DE 10 2011 009 867.4, filed on Jan. 31, 2011, all of which are incorporated herein by reference.

This patent application is also related to patent application Ser. No. 13/361,340 filed on Jan. 30, 2012, entitled "DIRECTLY APPLICABLE ELECTRICAL BUSHING"; patent application Ser. No. 13/361,348 filed on Jan. 30, 2012, entitled "IMPLANTABLE DEVICE HAVING AN INTEGRATED CERAMIC BUSHING"; patent application Ser. No. 13/361,355 filed on Jan. 30, 2012, entitled "HEAD PART FOR AN IMPLANTABLE MEDICAL DEVICE"; patent application Ser. No. 13/361,362 filed on Jan. 30, 2012, entitled "CERMET-CONTAINING BUSHING FOR AN IMPLANTABLE MEDICAL DEVICE HAVING A CONNECTING LAYER"; patent application Ser. No. 13/361,370 filed on Jan. 30, 2012, entitled "ELECTRICAL BUSHING WITH CERMET-CONTAINING CONNECTING ELEMENT FOR AN ACTIVE IMPLANTABLE MEDICAL DEVICE"; patent application Ser. No. 13/361,374 filed on Jan. 30, 2012, entitled "CERAMIC BUSHING WITH FILTER"; patent application Ser. No. 13/361,383 filed on Jan. 30, 2012, entitled "CERAMIC BUSHING WITH INDUCTIVE FILTER"; patent application Ser. No. 13/361,388 filed on Jan. 30, 2012, entitled "CERAMIC BUSHING HAVING HIGH CONDUCTIVITY CONDUCTING ELEMENTS"; patent application Ser. No. 13/361,398 filed on Jan. 30, 2012, entitled "METHOD FOR THE MANUFACTURE OF A CERMET-CONTAINING BUSHING"; patent application Ser. No. 13/361,404 filed on Jan. 30, 2012, entitled "METHOD FOR THE MANUFACTURE OF A CERMET-CONTAINING BUSHING FOR AN IMPLANTABLE MEDICAL DEVICE"; and patent application Ser. No. 13/361,411 filed on Jan. 30, 2012, entitled "CERMET-CONTAINING BUSHING WITH HOLDING ELEMENT FOR AN IMPLANTABLE MEDICAL DEVICE";

BACKGROUND

One aspect relates to an electrical bushing for use in a housing of an implantable medical device. Moreover, one aspect relates to a method for the manufacture of an electrical bushing for an implantable medical device.

The post-published document, DE 10 2009 035 972, discloses an electrical bushing for an implantable medical device having the features of the preamble of claim 1. Moreover, a use of at least one cermet-comprising conducting element in an electrical bushing for an implantable medical device and a method for the manufacture of an electrical bushing for an implantable medical device are disclosed.

A multitude of electrical bushings for various applications are known, examples including: U.S. Pat. No. 4,678,868, U.S. Pat. No. 7,564,674 B2, US 2008/0119906 A1, U.S. Pat. No. 7,145,076 B2, U.S. Pat. No. 7,561,917, US 2007/0183118 A1, US7260434B1, U.S. Pat. No. 7,761,165, U.S. Pat. No. 7,742,817 B2, U.S. Pat. No. 7,736,191 B1, US 2006/0259093 A1, U.S. Pat. No. 7,274,963 B2, US 2004116976 A1, U.S. Pat. No. 7,794,256, US 2010/0023086 A1, U.S. Pat. No. 7,502,217 B2, U.S. Pat. No. 7,706,124 B2, U.S. Pat. No. 6,999,818 B2, EP 1754511 A2, U.S. Pat. No. 7,035,076, EP 1685874 A1, WO 03/073450 A1, U.S. Pat. No. 7,136,273, U.S. Pat. No. 7,765,005, WO 2008/103166 A1, US 2008/0269831, U.S. Pat. No. 7,174,219 B2, WO 2004/110555 A1, U.S. Pat. No. 7,720,538 B2, WO 2010/091435, US 2010/0258342 A1, US 2001/0013756 A1, U.S. Pat. No. 4,315,054, and EP 0877400.

From DE 10 2008 021 064 A1 is known a connection housing for an electrical medical implant having contact sockets for accommodating and contacting electrode lead plugs. The connection housing includes a base module and a separately fabricated lid module, which is inserted into the base module and connected to it and has a contact socket that complies with the IS-4 standard.

From US 2008/0119906 A1 is known a hermetically sealed electrical bushing for cardiac pacemakers and defibrillators. Said bushing includes a flat ceramic disc that is used as an insulating support. The insulating disc includes openings, into which various electrodes are inserted as through-going contacts. Moreover, a metal flange is disclosed through which the ceramic disc can be connected to a housing.

From U.S. Pat. No. 7,260,434 is known a bushing device for an implantable medical device. It includes a plurality of filtered feedthrough arrangements each of which extends through an insulating base.

DE 697 297 19 T2 describes an electrical bushing for an active implantable medical device—also called implantable device or therapeutic device. Electrical bushings of this type serve to establish an electrical connection between a hermetically sealed interior and an exterior of the therapeutic device. Known implantable therapeutic devices are cardiac pacemakers or defibrillators, which usually includes a hermetically sealed metal housing which is provided with a connection body, also called header, on one of its sides. Said connection body includes a hollow space having at least one connection socket for connecting electrode leads. In this context, the connection socket includes electrical contacts in order to electrically connect the electrode leads to the control electronics on the interior of the housing of the implantable therapeutic device. Hermetic sealing with respect to a surrounding is an essential prerequisite of an electrical bushing of this type. Therefore, lead wires that are introduced into an electrically insulating base body, also called signal-transmission elements, through which the electrical signals are propagated, must be introduced into the base body such as to be free of gaps.

In this context, it has proven to be challenging that the lead wires generally are made of a metal and are introduced into a ceramic base body. In order to ensure durable connection between the two elements, the internal surface of a through-opening—also called openings—in the base body is metallized for attachment of the lead wires by soldering. However, the metallization in the through-opening has proven to be difficult to apply. Only expensive procedures ensure homogeneous metallization of the internal surface of the bore hole—and thus a hermetically sealed connection of the lead wires to the base body by soldering. The soldering process itself requires additional components, such as solder rings. Moreover, the process of connecting the lead wires to the previously metallized insulators utilizing the solder rings is a process that is laborious and difficult to automate.

For these and other reasons there is a need for the present invention.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Further measures and advantages of the invention are evident from the claims, the description provided hereinafter, and the drawings. The invention is illustrated through several exemplary embodiments in the drawings. In this context, equal or functionally equal or functionally corresponding elements are identified through the same reference numbers. The invention shall not be limited to the exemplary embodiments.

DETAILED DESCRIPTION

Figure 1:
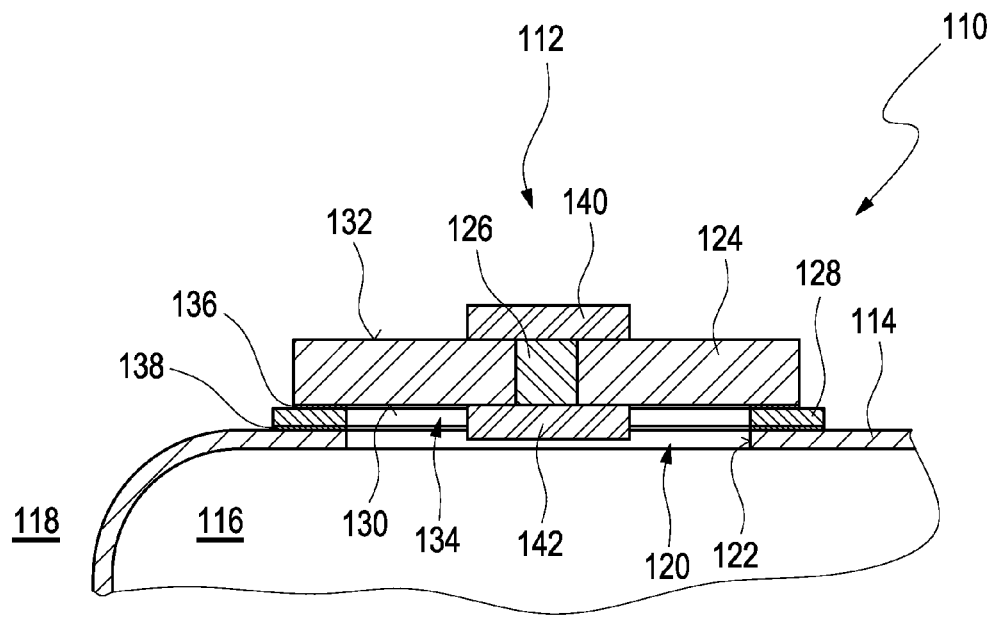
FIGS. 1 and 2 illustrate implantable medical devices according various exemplary embodiments and electrical bushings according to various embodiments.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

One aspect specifies an electrical bushing for use in a housing of an implantable medical device, which circumvents the disadvantages of known devices of the above-mentioned type at least in part. For example, an electrical bushing for use in a housing of an implantable medical device is to be proposed that is easy to manufacture, highly sealed, and, furthermore, enables external components to be connected easily.

Other aspects propose an electrical bushing for use in a housing of an implantable medical device, an implantable medical device, a method for the manufacture of an electrical bushing, and a method for the manufacture of an implantable medical device having the features of the independent claims. Refinements of the embodiments, which can be implemented alone or in combination, are specified in the dependent claims. Features and details that are described in the context of the electrical bushing or the implantable device shall also apply in relation to the respective methods, and vice versa.

In summary, the following embodiments are proposed:

Embodiment 1

Electrical bushing for use in a housing of an implantable medical device, whereby the electrical bushing includes at least one electrically insulating base body and at least one electrical conducting element;

whereby the conducting element is set up to establish, through the base body, at least one electrically conductive connection between an internal space of the housing and an external space;

whereby the conducting element is hermetically sealed, at least in part, with respect to the base body;

whereby the at least one conducting element includes at least one cermet;

characterized in that the electrical bushing includes at least one metallic frame element, whereby the frame element is set up to fix the base body in at least one housing opening of the housing.

Embodiment 2

Electrical bushing according to the preceding embodiment, characterized in that the frame element includes at least one metallic material selected from the group consisting of: titanium; a titanium alloy; niobium; a niobium alloy; platinum; a platinum alloy; iridium; molybdenum; tantalum; a tantalum alloy; tungsten; a tungsten alloy; stainless steel; a cobalt-chromium alloy.

Embodiment 3

Electrical bushing according to any one of the preceding embodiments, characterized in that the frame element includes at least one frame opening that is surrounded at least in part and fully by the frame element, whereby the frame element is connected to the base body in a manner such that the base body and the conducting element close the frame opening in a hermetically sealed manner.

Embodiment 4

Electrical bushing according to the preceding embodiment, characterized in that the base body projects into the frame opening, at least in part, and fills the frame opening, at least in part.

Embodiment 5

Electrical bushing according to either one of the two preceding embodiments, characterized in that the frame opening has a cross-section selected from the group consisting of: a round cross-section, an oval cross-section, a polygonal cross-section.

Embodiment 6

Electrical bushing according to any one of the preceding embodiments, characterized in that the frame element and the base body are shaped to be acting in concert such that the base body can be unambiguously positioned, for example, can be centered, with respect to the frame element when the base body is being connected to the frame element, for example, in that the frame element surrounds at least a part of the base body in a ring-shaped manner.

Embodiment 7

Electrical bushing according to any one of the preceding embodiments, whereby the base body includes at least one first section that projects into a frame opening of the frame element and is surrounded by the frame element at least in part, for example, in ring-shaped manner, whereby the base body further includes at least one second section that projects out of the frame opening.

Embodiment 8

Electrical bushing according to the preceding embodiment, whereby the second section has a larger diameter or equivalent diameter than the first section.

Embodiment 9

Electrical bushing according to any one of the preceding embodiments, characterized in that the frame element is connected to the base body through at least one firmly bonded connection, for example, through at least one soldered connection and/or at least one welded connection.

Embodiment 10

Electrical bushing according to the preceding embodiment, characterized in that the base body includes at least one metallization at least in a region that faces the firmly bonded connection, for example, at least one metallization comprising at least one metal selected from the group consisting of gold, titanium, and chromium and/or at least one combination and/or at least one multi-layer comprising one or more of said metals.

Embodiment 11

Electrical bushing according to any one of the preceding embodiments, characterized in that the frame element, at least parts thereof, is provided as an annular disc, for example, as an annular disc with a round, oval or polygonal cross-section.

Embodiment 12

Electrical bushing according to the preceding embodiment, whereby the base body is placed on the annular ring on a side that faces an internal space of the housing or an external space of the housing.

Embodiment 13

Electrical bushing according to any one of the preceding embodiments, characterized in that the frame element includes, on at least one side that faces the housing, at least one fastening profile and is provided, for example, as flange.

Embodiment 14

Electrical bushing according to the preceding embodiment, characterized in that the fastening profile has a cross-section selected from the group consisting of: a U-shaped profile; an L-shaped profile; an H-shaped profile; a T-shaped profile.

Embodiment 15

Electrical bushing according to any one of the preceding embodiments, characterized in that the conducting element and the base body are connected in a firmly bonded manner, for example, through a firmly bonded sintered connection.

Embodiment 16

Electrical bushing according to any one of the preceding embodiments, characterized in that the conducting element is embedded in the base body, at least in part.

Embodiment 17

Electrical bushing according to any one of the preceding embodiments, characterized in that the cermet includes at least one metallic component, whereby the metallic component is selected from the group consisting of: platinum, a platinum alloy, iridium, niobium, molybdenum, titanium, a titanium alloy, cobalt, zirconium, chromium, tantalum, a tantalum alloy, tungsten, a tungsten alloy.

Embodiment 18

Electrical bushing according to any one of the preceding embodiments, characterized in that the cermet includes at least one ceramic component selected from the group consisting of: aluminum oxide, for example, $Al_2O_3$; zirconium oxide, for example, $ZrO_2$; magnesium oxide, for example, MgO; ZTA; ATZ; Y-TZP; aluminum nitride; aluminum titanate; a piezoceramic material, for example, a lead-free piezoceramic material selected from the group consisting of Ba $(Zr, Ti)O_3$, Ba $(Ce, Ti)O_3$, KNN, KNN—$LiSbO_3$, and KNN—$LiTaO_3$.

Embodiment 19

Electrical bushing according to any one of the preceding embodiments, characterized in that the electrical bushing includes at least 2 conducting elements, for example, at least 4 conducting elements, and in another example, at least 10 conducting elements.

Embodiment 20

Electrical bushing according to any one of the preceding embodiments, characterized in that the base body is made, at least in part, from an insulating composition of materials, for example, from a insulating composition of materials.

Embodiment 21

Electrical bushing according to the preceding embodiment, characterized in that the insulating composition of materials is selected from the group consisting of: aluminum oxide, for example, $Al_2O_3$; zirconium oxide, for example, $ZrO_2$; magnesium oxide, for example, MgO; ZTA; ATZ; Y-TZP; aluminum nitride; aluminum titanate; a piezoceramic material, for example, a lead-free piezoceramic material selected from the group consisting of Ba $(Zr, Ti)O_3$, Ba $(Ce, Ti)O_3$, KNN, KNN—$LiSbO_3$, and KNN—$LiTaO_3$.

Embodiment 22

Electrical bushing according to any one of the preceding embodiments, characterized in that the electrical bushing further includes at least one filter element, for example, a filter element selected from the group consisting of: a high-pass filter, a low-pass filter, a band-pass filter.

Embodiment 23

Implantable medical device, comprising at least one housing with at least one housing opening and at least one electrical bushing according to any one of the preceding embodiments, whereby the electrical bushing is connected to the housing by means of the at least one frame element, whereby the electrical bushing establishes at least one electrical connection between at least one internal space of the housing and at least one external space.

Embodiment 24

Implantable medical device according to the preceding embodiment, whereby the housing opening is closed through the electrical bushing in a hermetically sealed manner.

Embodiment 25

Implantable medical device according to any one of the preceding embodiments that are related to an implantable medical device, whereby the frame element is connected to the housing in a firmly bonded manner, for example, through at least one soldered connection and/or one welded connection.

Embodiment 26

Implantable medical device according to any one of the preceding embodiments that are related to an implantable medical device, characterized in that the frame element is connected to at least one region of the housing selected from the group consisting of: an external side of the housing facing an external space of the housing; an internal side of the housing facing an internal side of the housing; a rim of the housing that surrounds the housing opening, at least in part.

Embodiment 27

Implantable medical device according to any one of the preceding embodiments that are related to an implantable medical device, characterized in that the implantable medical device is selected from the group consisting of: an active implantable device for transmitting an electrical stimulation to a body tissue, for example, a muscle, a nerve, a brain region or a blood vessel; a cardiac pacemaker; an implantable defibrillator; a device against congestive heart failure; a hearing aid; a cochlea implant; a retina implant; a neurostimulator; a peripheral muscle stimulator; a drug pump, for example, an insulin pump; a ventricular aiding device; a spinal marrow stimulator; an implantable sensor system; an artificial heart; an incontinence device; a bone growth stimulator; a gastric pacemaker; a prosthetic device.

Embodiment 28

Method for the manufacture of an electrical bushing according to any one of the preceding embodiments that are related to an electrical bushing, characterized in that the method includes the following steps:

a. manufacturing the at least one base body and introducing the at least one conducting element into the base body in non-sintered or pre-sintered condition;

b. joint sintering of the base body and conducting element;

c. connecting the base body to the at least one frame element.

Embodiment 29

Method for the manufacture of an implantable medical device, for example, of an implantable medical device according to any one of the preceding embodiments that are related to an implantable medical device, whereby the implantable medical device includes at least one housing, characterized in that the method includes the following steps:

i. manufacturing at least one electrically insulating base body and at least one electrical conducting element, whereby the conducting element is hermetically sealed, at least in part, with respect to the base body, whereby the conducting element is being set up to establish, through the base body, at least one electrically conductive connection between an internal space of the housing and an external space, and whereby the at least one conducting element includes at least one cermet;

ii. connecting at least one metallic frame element to the base body, whereby the frame element is set up to fix the base body in at least one housing opening of the housing, whereby, for example, an electrical bushing according to any one of the preceding embodiments that are related to an electrical bushing is formed;

iii. connecting the frame element to the housing.

The proposed electrical bushing is set up for use in an implantable medical device, that is, for application in an implantable medical device, whereby the implantable medical device can be provided, for example, as an active implantable medical device (AIMD) and as a therapeutic device.

As a general rule, the term, implantable medical device, shall include any device which is set up to perform at least one medical function and can be introduced into a body tissue of a human or animal user. As a general rule, the medical function can include any function selected from the group consisting of a therapeutic function, a diagnostic function, and a surgical function. In one example, the medical function can include at least one function, in which at least one stimulus is exerted on the body tissue, for example, an electrical stimulus. Said function of exerting a stimulus can be exerted, for example, through at least one stimulator and/or through at least one stimulus transmitter, for example through at least one actuator. However, other types of exerting a stimulus are also feasible as a matter of principle.

As a matter of principle, the term, active implantable medical device—also called AIMD—includes all implantable medical devices that can conduct electrical signals from a hermetically sealed housing to a part of the body tissue of the user and/or receive electrical signals from the part of the body tissue of the user. Accordingly, the term, active implantable medical device, includes, for example, cardiac pacemakers, cochlea implants, implantable cardioverters/defibrillators, nerve, brain, organ or muscle stimulators as well as implantable monitoring devices, hearing aids, retinal implants, muscle stimulators, implantable drug pumps, artificial hearts, bone growth stimulators, prostate implants, stomach implants or the like. Refinements are specified in embodiment 27 specified above.

The implantable medical device, for example, the active implantable medical device, includes at least one housing, for example, at least one hermetically sealed housing. The housing can enclose at least one electronics unit, for example a triggering and/or analytical electronics unit of the implantable medical device.

According to one embodiment, a housing of an implantable medical device shall be understood to be an element that encloses, at least in part, at least one functional element of the implantable medical device that is set up to perform the at least one medical function or promotes the medical function. For example, the housing includes at least one internal space that takes up the functional element fully or in part. For example, the housing can be set up to provide mechanical protection to the functional element with respect to strains occurring during operation and/or upon handling, and/or provide protection to the functional element with respect to ambient influences such as, for example, influences of a body fluid. The housing can, for example, border and/or close the implantable medical device with respect to the outside.

In this context, an internal space shall be understood herein to mean a region of the implantable medical device, for example, within the housing, which can take up the functional element fully or in part and which, in an implanted state, does not contact the body tissue and/or a body fluid. The internal space can includes at least one hollow space which can be closed fully or in part. However, alternatively, the internal space can be filled up fully or in part, for example by the at least one functional element and/or by at least one filling material, for example at least one casting, for example at least one casting material in the form of an epoxy resin or a similar material.

An external space, in contrast, shall be understood to be a region outside of the housing. This can, for example, be a region which, in the implanted state, can contact the body tissue and/or a body fluid. Alternatively or in addition, the external space can just as well be or include a region that is only accessible from outside the housing without necessarily contacting the body tissue and/or the body fluid, for example a region of a connecting element of the implantable medical device that is accessible from outside to an electrical connecting element, for example an electrical plug connector.

The housing and/or, for example, the electrical bushing can, for example, be provided to be hermetically sealed such that, for example, the internal space, is hermetically sealed with respect to the external space. In this context, the term, "hermetically sealed", can illustrate that moisture and/or gases cannot permeate through the hermetically sealed element at all or only to a minimal extent upon the intended use for the common periods of time (for example 5-10 years). The so-called leak rate, which can be determined, for example, by leak tests, is a physical parameter that can describe, for example, a permeation of gases and/or moisture through a device, for example, through the electrical bushing and/or the housing. Pertinent leak tests can be carried out with helium leak testers and/or mass spectrometers and are specified in the Mil-STD-883G Method 1014 standard. In this context, the maximal permissible helium leak rate is determined as a function of the internal volume of the device to be tested. According to the methods specified in MIL-STD-883G, method 1014, section 3.1 and taking into consideration the volumes and cavities of the devices to be tested that are used in the application of the present embodiment, said maximal permissible helium leak rates can, for example, be from $1\times10^{-8}$ atm*cm$^3$/sec to $1\times10^{-7}$ atm*cm$^3$/sec. In the scope of one embodiment, the term, "hermetically sealed", shall be understood, for example, to mean that the device to be tested (for example the housing and/or the electrical bushing and/or the housing with the electrical bushing) has a helium leak rate of less than $1\times10^{-7}$ atm*cm$^3$/sec. In one embodiment, the helium leak rate can be less than $1\times10^{-8}$ atm*cm$^3$/sec, for example, less than $1\times10^{-9}$ atm*cm$^3$/sec. For the purpose of standardization, the above-mentioned helium leak rates can also be converted into the equivalent standard air leak rate. The definition of the equivalent standard air leak rate and the conversion are specified in the ISO 3530 standard.

Electrical bushings are elements set up to create at least one electrically conductive path that extends between the internal space of the housing to at least one external point or region outside the housing, for example, situated in the external space. Accordingly, this establishes, for example, an electrical connection to leads, electrodes, and sensors that are arranged outside the housing.

Common implantable medical devices are commonly provided with a housing, which can include, on one side, a head part, also called header or connecting body, that carries connection sockets for connection of leads, also called electrode leads. The connection sockets include, for example, electrical contacts that serve to electrically connect the leads to a control electronics unit on the interior of the housing of the medical device. Usually, an electrical bushing is provided in the location, at which the electrical connection enters into the housing of the medical device, and the electrical bushing is inserted into a corresponding opening of the housing in a hermetically sealing manner.

Due to the type of use of implantable medical devices, their hermetic sealing and biocompatibility are usually amongst the foremost requirements. The implantable medical device proposed herein according to one embodiment, can be inserted, for example, into a body of a human or animal user, for example, of a patient. As a result, the implantable medical device is usually exposed to a fluid of a body tissue of the body. Accordingly, it is usually important that no body fluid penetrates into the implantable medical device and that no liquids leak from the implantable medical device. In order to ensure this, the housing of the implantable medical device, and thus the electrical bushing as well, should be as impermeable as possible, for example, with respect to body fluids.

Moreover, the electrical bushing should ensure high electrical insulation between the at least one conducting element and the housing and/or the multiple conducting elements provided that more than one conducting element are present. In this context, the insulation resistance reached is at least several MOhm, for example, more than 20 MOhm, and the leakage currents reached can be small, for example, less than 10 pA. Moreover, in case multiple conducting elements are present, the crosstalk and electromagnetic coupling between the individual conducting elements are below the specified thresholds for medical applications.

The electrical bushing disclosed according to one embodiment is well-suited for the above-mentioned applications. Moreover, the electrical bushing can also be used in other applications that are associated with special requirements with regard to biocompatibility, tight sealing, and stability.

The electrical bushing according to one embodiment can meet, for example, the above-mentioned tight sealing requirements and/or the above-mentioned insulation requirements.

The electrical bushing can basically take any shape, for example a round shape, an oval shape or a polygonal shape, for example, a rectangular or square shape, for example in a viewing direction towards a housing opening of the housing.

As mentioned above, the electrical bushing includes at least one electrically insulating base body. In one embodiment, a base body shall be understood to mean an element that serves a mechanical holding function in the electrical bushing, for example in that the base body holds or carries the at least one conducting element either directly or indirectly. For example, the at least one conducting element can be embedded in the base body directly or indirectly, fully or partly, for example, through a firmly bonded connection between the base body and the conducting element and in one example through co-sintering of the base body and the conducting element. For example, the base body can have at least one side facing the internal space and at least one side facing the external space and/or accessible from the external space.

The base body can, for example, be designed to be rotationally symmetrical about an axis, for example about an axis that is arranged to be essentially perpendicular to the housing opening. Accordingly, the base body can have the shape of a disc, for example a disc with a round, oval or polygonal base surface. Alternatively, the base body may just as well have a graduated shape, for example a shape of at least two discs of different diameters or equivalent diameters that are placed one on the other, which in one embodiment are in a concentric arrangement with respect to each other and which, for example, can have a round, an oval or a polygonal, for example, rectangular or square, cross-section. However, other designs are also feasible as a matter of principle.

As mentioned above, the base body is provided to be electrically insulating. This means that the base body, fully or at least regions thereof, is made from at least one electrically insulating material. For example, the at least one electrically insulating material can be arranged such that the at least one conducting element is electrically insulated with respect to the housing and/or, if multiple conducting elements are provided, that these are electrically insulated with respect to each other. In this context, an electrically insulating material shall be understood to mean a material with a resistivity of at least $10^2$ Ohm*m, for example, of at least $10^6$ Ohm*m, for example, of at least $10^{10}$ Ohm*m, and for example, of at least $10^{12}$ Ohm*m. For example, the base body can be provided such that, as mentioned above, a flow of current between the conducting element and the housing and/or between multiple conducting elements is prevented, at least largely, for example through the resistivity values between the conducting element and the housing as specified above being implemented. For example, the base body can include at least one ceramic material.

In this context, a conducting element or electrical conducting element shall generally be understood to mean an element set up to establish an electrical connection between at least two sites and/or at least two elements. For example, the conducting element can include one or more electrical conductors, for example metallic conductors. In the scope of one embodiment, the conducting element is made fully or partly of at least one cermet, as mentioned above. In addition, one or more other electrical conductors, for example metallic conductors, can be provided. The conducting element can, for example, be provided in the form of one or more contact pins and/or curved conductors. Moreover, the conducting element can include, for example, on a side of the base body and/or electrical bushing facing the internal space or on a side of the base body and/or electrical bushing facing the external space or accessible from the external space, one or more connecting contacts, for example one or more plug-in connectors, for example one or more connecting contacts, which project from the base body or can be electrically contacted through other means from the internal space and/or the external space. The conducting element can, for example, can, on the side of the base body facing the internal space, end flush with the base body and/or project from the base body into the internal space or be connected to another element. Regardless of the design of the inside, this applies just as well to the side of the base body facing the external space.

The at least one conducting element can be electrically connected within the base body and/or on a side of the base body that faces the internal space and/or on a side of the base body that faces the external space, to one or more conductor elements. For example, one or more wires can be provided. The at least one conductor element can be manufactured, for example, fully or in part from at least one metallic material selected from the group consisting of: platinum; a platinum alloy; iridium; niobium; molybdenum; titanium; a titanium alloy; tantalum; a tantalum alloy; tungsten; a tungsten alloy; stainless steel; a cobalt-chromium alloy; gold; a gold alloy; silver; a silver alloy; copper; a copper alloy, aluminum, an aluminum alloy. Combinations of the specified materials and/or other materials are feasible just as well.

The at least one conducting element can establish the electrically conductive connection between the internal space and the external space in a variety of ways. For example, the conducting element can extend from at least one section of the conducting element that is arranged on the side of the base body facing the internal space to at least one section of the conducting element arranged on the side facing the external space or accessible from the external space. However, other arrangements are also feasible as a matter of principle. Accordingly, the conducting element can just as well include a plurality of partial conducting elements that are connected to each other in an electrically conducting manner. Moreover, the conducting element can extend into the internal space and/or the external space. For example, the conducting element can include at least one region that is arranged in the internal space and/or at least one region that is arranged in the external space, whereby the regions can, for example, be electrically connected to each other.

In the scope of one embodiment, a frame element shall be understood to mean an element set-up to serve as connecting element between the base body and the housing and to allow the base body to be fixed in place in or on the housing. The fixation can be effected fully or partly inside and/or outside the housing and/or partly or fully within the opening of the housing. All of the options mentioned shall be included by the formulation of the fixation in the at least one housing opening of the housing specified in embodiment 1. The housing opening, in turn, can have any cross-section as a matter of principle, for example a round, oval or polygonal shape, for example, a rectangular or square shape. For example, the frame element can be designed such as to effect a connection between the base body and the housing to be hermetically sealed, for example, in such a manner that the housing opening is closed and the frame element is hermetically sealed through the base body.

As mentioned above, the frame element is designed as a metallic frame element, that is, it is fully or partly made from at least one metallic material. In one embodiment, the frame element is free of ceramic materials. The frame element can consist, for example, fully or partly of one or more of the materials specified in embodiment 2 above. However, a combination of the materials specified and/or other materials shall also be feasible.

The frame element can, for example, surround the base body fully or in part. Accordingly, the frame element can, for example, be ring-shaped having at least one frame opening, into which the base body can project for example, or in which the base body is taken up fully or partly for example, and which is hermetically sealed through the base body.

The electrically insulating base body can support, as a bearing, and/or surround, at least in part, for example, the at least one conducting element. In one example, the at least one conducting element can be embedded in the base body fully or partly, for example in a firmly bonded manner. In one embodiment, the at least one material of the base body should be biocompatible, as illustrated above, and should have sufficiently high insulation resistance. It has proven to be advantageous for the base body according to one embodiment to include at least one ceramic material or to consist of at least one ceramic material. In one embodiment, the base body includes one or more materials selected from the group consisting of: aluminum oxide ($Al_2O_3$), zirconium dioxide ($ZrO_2$), aluminum oxide-toughened zirconium oxide (ZTA), zirconium oxide-toughened aluminum oxide (ZTA—Zirconia Toughened Aluminum—$Al_2O_3/ZrO_2$), yttrium-toughened zirconium oxide (Y-TZP), aluminum nitride (AlN), magnesium oxide (MgO), piezoceramic materials, barium (Zr, Ti) oxide, barium (CE, Ti) oxide, and sodium-potassium-niobate.

With regard to possible refinements of the cermet and/or metal materials and/or components that are used, reference shall be made to the embodiments specified above. Combinations of multiple possibilities specified above are conceivable as well. In this context, ZTA shall be understood to mean zirconium-toughened alumina (Zirkonia Toughened Alumina), that is, a material, in which zirconium oxide is embedded in an aluminum oxide matrix, for example 10-30% by volume zirconium dioxide in an aluminum oxide matrix. In this context, ATZ shall be understood to mean alumina-toughened zirconia, that is, a material, in which aluminum oxide is embedded in a zirconium oxide matrix, for example at a fraction of 10-30% by volume. Y-TZP shall be understood to mean yttrium-toughened zirconium oxide, that is, zirconium oxide comprising an yttrium fraction. KNN means potassium-sodium niobate.

The base body can, for example, be made fully or partly from one or more sinterable materials, for example, from one or more ceramic-based sinterable materials. The conducting element or elements can fully or partly be made of one or more cermet-based sinterable materials. Moreover, the at least one conducting element can also, as mentioned above, include one or more additional conductors, for example one or more metallic conductors with no ceramic fraction.

In the scope of one embodiment, "cermet" shall refer to a composite material made of one or more ceramic materials in at least one metallic matrix or a composite material made of one or more metallic materials in at least one ceramic matrix. For production of a cermet, for example, a mixture of at least one ceramic powder and at least one metallic powder can be used to which, for example, at least one binding agent and, if applicable, at least one solvent can be added. The ceramic powder or powders of the cermet in one embodiment have a mean grain size of less than 10 µm, in one embodiment less than 5 µm, and in one embodiment less than 3 µm. The metallic powder or powders of the cermet in one embodiment have a mean grain size of less than 15 µm, in one embodiment less than 10 µm, and in one embodiment less than 5 µm. For production of a base body, for example, at least one ceramic powder can be used to which, for example, at least one binding agent and, if applicable, at least one solvent can be added. In this context, the ceramic powder or powders in one embodiment has/have a mean grain size of less than 10 µm (1 µm is equal to $1 \times 10^{-6}$ m), in one embodiment less than 5 µm, in one embodiment less than 3 µm. For example, the median value or the d50 value of the grain size distribution is considered to be the mean grain size in this context. The d50 value corresponds to the value at which 50 percent of the grains of the ceramic powder and/or metallic powder are finer and 50% are coarser than the d50 value.

In the scope of one embodiment, a ceramic manufacturing method shall be understood to mean a procedure that includes at least one sintering process of at least one insulating and/or at least one electrically conductive material, for example, at least one ceramic material. As shall be explained in more detail below, said ceramic manufacturing method can, for example, include a forming for the manufacture of at least one form body, for example one ceramic green compact and/or at least one ceramic brown compact.

In the scope of one embodiment, a sintering or a sintering process shall generally be understood to mean a procedure for the manufacture of materials or work-pieces, in which powdered, for example, fine-grained, ceramic and/or metallic substances are heated and connected in the process. This process can proceed without applying external pressure onto the substance to be heated or can, for example, proceed under elevated pressure onto the substance to be heated, for example under a pressure of at least 2 bar, in one embodiment higher pressures, for example pressures of at least 10 bar, in one embodiment at least 100 bar, or even at least 1000 bar. The process can proceed, for example, fully or partly, at temperatures below the melting temperature of the powdered materials, for example at temperatures of 700° C. to 1400° C. The process can be carried out, for example, fully or partly, in a tool and/or a mold such that a forming step can be associated with the sintering process. Aside from the powdered materials, a starting material for the sintering process can include further materials, for example one or more binding agents and/or one or more solvents. The sintering process can proceed in one or more steps, whereby additional steps can precede the sintering process, for example one or more forming steps and/or one or more debinding steps.

Accordingly, a sintered condition is understood to mean a condition of a work-piece, in which the work-piece has already undergone one or more steps of sintering. Accordingly, a non-sintered condition is understood to mean a condition, in which the work-piece has not yet undergone a step of sintering. In this condition, the work-piece can for example be present as a green compact. A pre-sintered condition shall be understood to mean a condition, in which the work-piece has already undergone at least one step of sintering or at least one part of a step of sintering, in which the work-piece has not been sintered completely though, that is, in which the work-piece can still be sintered further and can be sintered further through one or more steps of sintering. In this condition, the work-piece can be present, for example, as at least partial green compact, as brown compact or already as a ceramic body.

A method can be used, for example, in the manufacture of the at least one conducting element and/or optionally in the manufacture of the at least one base body, in which at least one green compact is manufactured first, subsequently at least one brown compact is manufactured from said green compact, and subsequently the finished work-piece is manufactured from said brown compact through at least one sintering step. In this context, separate green compacts and/or separate brown compacts can be manufactured for the conducting element and the base body and can be connected subsequently. Alternatively, one or more common green compacts and/or brown compacts can be produced for the base body and the conducting element. Alternatively again, separate green compacts can be produced first, said green compacts can then be connected, and subsequently a common brown compact can be produced from the connected green compact. In general, a green compact shall be understood to mean a pre-form body of a work-piece which includes the starting material, for example the at least one ceramic and/or metallic powder, as well as, if applicable, one or more binding materials. A brown compact shall be understood to mean a pre-form body which is generated from the green compact through at least one debinding step, for example at least one thermal and/or chemical debinding step, whereby the at least one binding agent and/or the at least one solvent is/are removed, at least partly, from the pre-form body in the debinding step.

The sintering process, for example, of a cermet, but of the base body just as well, for example, can proceed comparable to a sintering process that is commonly used for homogeneous powders. For example, the material can be compacted in the sintering process at high temperature and, if applicable, high pressure such that the cermet is virtually sealed tight or has no more than closed porosity. Usually, cermets are characterized by their particularly high toughness and wear resistance. Compared to sintered hard metals, a cermet-containing transmission element usually has a higher thermal shock and oxidation resistance and usually a thermal expansion coefficient that is matched to a surrounding insulator.

For the bushing according to one embodiment, the at least one ceramic component of the cermet can include, for example, at least one of the following materials: aluminum oxide ($Al_2O_3$), zirconium dioxide ($ZrO_2$), aluminum oxide-toughened zirconium oxide (ZTA), zirconium oxide-toughened aluminum oxide (ZTA—Zirconia Toughened Aluminum—$Al_2O_3/ZrO_2$), yttrium-toughened zirconium oxide (Y-TZP), aluminum nitride (AlN), magnesium oxide (MgO), piezoceramic materials, barium (Zr, Ti) oxide, barium (CE, Ti) oxide, and sodium-potassium-niobate.

For the bushing according to one embodiment, the at least one metallic component of the cermet can include, for example, at least one of the following metals and/or an alloy based on at least one of the following metals: platinum, iridium, niobium, molybdenum, tantalum, tungsten, titanium, cobalt or zirconium. An electrically conductive connection is usually established in the cermet when the metal content exceeds the so-called percolation threshold at which the metal particles in the sintered cermet are connected to each other, at least in spots, such that electrical conduction is enabled. For this purpose, experience tells that the metal content should be 25% by volume and more, in one embodiment 32% by volume, in one embodiment more than 38% by volume, depending on which materials have been selected.

In the scope of one embodiment, the terms, "including a cermet," "comprising a cermet," and "cermet-containing", are used synonymously. Accordingly, the terms refer to the property of an element, being that the element contains cermet. This meaning also includes the variant of an embodiment in that the element, for example the conducting element, consists of a cermet, that is, is fully made of a cermet.

In one embodiment, both the at least one conducting element and the base body can include one or more components which are or can be manufactured in a sintering procedure, or the at least one conducting element and the base body are or can both be manufactured in a sintering procedure. In one embodiment, the base body and the conducting element are or can be manufactured in a co-sintering procedure, that is, a procedure of simultaneous sintering of these elements. For example, the conducting element and the base body each can include one or more ceramic components that are manufactured, and compacted, in the scope of at least one sintering procedure.

For example, a base body green compact can be manufactured from an insulating composition of materials. This can proceed, for example, by compressing the composition of materials in a mold. In this context, the insulating composition of materials advantageously is a powder mass, in which the powder particles show at least minimal cohesion. In this context, the manufacture of a green compact proceeds, for example, through compressing powder masses and/or through forming followed by drying.

Said procedural steps can also be utilized to form at least one cermet-containing conducting element green compact. In this context, one embodiment can provide that the powder, which is compressed to form the conducting element green compact, is cermet-containing or consists of a cermet or includes at least one starting material for a cermet. Subsequently, the two green compacts—the base body green compact and the conducting element green compact—can be combined. The manufacture of the conducting element green compact and of the base body green compact can just as well proceed simultaneously, for example, by multi-component injection molding, co-extrusion, etc., such that there is no longer a need to connect them subsequently.

While the green compacts are being sintered, they are subjected to a heat treatment below the melting temperature of the powder particles of the green compact. This usually leads to compaction of the material and ensuing substantial reduction of the porosity and volume of the green compacts. Accordingly, one aspect of the method is that the base body and the conducting element can be sintered jointly. Accordingly, there is no longer a need to connect the two elements subsequently.

Through the sintering, the conducting element becomes connected to the base body in a positive fit-type and/or non-positive fit-type and/or firmly bonded manner. In one embodiment, this achieves hermetic integration of the conducting element into the base body. In one embodiment, there is no longer a need for subsequent soldering or welding of the conducting element into the base body. Rather, a hermetically sealing connection between the base body and the conducting element is attained through the joint sintering and utilization of a cermet-containing green compact.

One refinement of the method according to one embodiment is characterized in that the sintering includes only partial sintering of the at least one optional base body green compact, whereby said partial sintering can effect and/or include, for example, the debinding step described above. In one embodiment, the green compact is heat-treated in the scope of said partial sintering. This is usually already associated with some shrinkage of the volume of the green compact. However, the volume of the green compact has not yet reached its final state. Rather, another heat treatment is usually needed—a final sintering—in which the green compact(s) is/are shrunk to its/their final size. In the scope of said variant of an embodiment, the green compact is sintered only partly in order to attain a certain stability to render the green compact easier to handle.

The starting material used for producing at least one conducting element green compact and/or at least one base body green compact can, for example, be a dry powder or include a dry powder, whereby the dry powder is compressed in the dry state into a green compact and shows sufficient adhesion to maintain its compressed green compact shape. However, optionally, the starting material can include one or more further components in addition to the at least one powder, for example, as mentioned above, one or more binding agents and/or one or more solvents. Said binding agents and/or solvents, for example organic and/or inorganic binding agents and/or solvents, are generally known to the person skilled in the art, and are commercially available, for example. The starting material can, for example, include one or more slurries or be a slurry. In the scope of one embodiment, a slurry is a suspension of particles of a powder made of one or more materials in a liquid binding agent, and, if applicable, in a water-based or organic binding agent. A slurry has a high viscosity and can easily be shaped into a green compact without the application of high pressure.

In the case of green compacts made from slurries, the sintering process, which is generally carried out below the melting temperature of the ceramic, cermet or metal materials that are used, but in individual cases can also be carried out just above the melting temperature of the lower melting component of a multi-component mixture, this usually being the metal component, leads to the binding agent slowly diffusing from the slurry. Overly rapid heating leads to a rapid increase of the volume of the binding agent by transition to the gas phase and destruction of the green compact or formation of undesired defects in the workpiece.

Thermoplastic and duroplastic polymers, waxes, thermogelling substances and/or surface-active substances, for example, can be used as binding agent—also called binder. In this context, these can be used alone or as binding agent mixtures of multiple components of this type. If individual elements or all elements of the electrical bushing (for example the at least one base body green compact and/or the at least one conducting element green compact) are produced in the scope of an extrusion procedure, the composition of the binding agent should be such that the line of the elements extruded through the nozzle is sufficiently stable in shape for the shape defined by the nozzle to be maintained easily. Suitable binders, also called binding agents, are known to the person skilled in the art.

In contrast, the conducting element according to the prior art usually is a metal wire. A conducting element provided according to one embodiment with at least one cermet can be connected easily to other structural elements, since it is a composite of metal and ceramic material. Accordingly, green compacts of both the conducting element and other structural elements, for example in the base body, can be produced and subsequently subjected to a sintering process. Alternatively or in addition, at least one common green compact for multiple structural elements can be manufactured just as well. The resulting electrical bushing is not only particularly biocompatible and durable, but also possesses good hermetic sealing properties. Thus, usually no fissures or connecting sites still to be soldered arise between the conducting element and the base body. Rather, sintering results in the base body and the conducting element becoming connected. In one variant of an embodiment, the at least one conducting element consists of a cermet. In this variant of an embodiment, the conducting element includes not only components made of cermet, but is fully made of a cermet.

Generally, cermets are characterized by their particularly high toughness and wear resistance. The "cermets" and/or "cermet-containing" substances can, for example, be or include cutting materials related to hard metals which can dispense with tungsten carbide as the hard substance and can be produced, for example, by a powder metallurgical route. A sintering process for cermets and/or the cermet-containing bearing element can proceed, for example, alike a process for homogeneous powders except that, at identical compression force, the metal is usually compacted more strongly than the ceramic material. Compared to sintered hard metals, the cermet-containing conducting element usually shows higher resistance to thermal shock and oxidation. As explained above, the ceramic components can include, for example, at least one of the following materials: aluminum oxide ($Al_2O_3$), zirconium dioxide ($ZrO_2$), aluminum oxide-toughened zirconium oxide (ZTA), zirconium oxide-toughened aluminum oxide (ZTA—Zirconia Toughened Aluminum—$Al_2O_3/ZrO_2$), yttrium-toughened zirconium oxide (Y-TZP), aluminum nitride (AlN), magnesium oxide (MgO), piezoceramic materials, barium (Zr, Ti) oxide, barium (CE, Ti) oxide, and sodium-potassium-niobate. The at least one metallic component can include, for example, at least one of the following metals and/or an alloy based on at least one of the following metals: platinum, a platinum alloy, iridium, niobium, molybdenum, titanium, a titanium alloy, cobalt, zirconium, chromium, tantalum, a tantalum alloy, tungsten, a tungsten alloy.

As described above, there are multiple ways of connecting the electrical bushing to the housing. These options can also be combined with each other. Accordingly, one option is to directly connect the electrical bushing to the housing, for example in a positive fit-type manner and/or non-positive fit-type manner and/or firmly bonded manner. For example, a firmly bonded connection between the frame element and an inside and/or an outside of the housing and/or an edge of the housing facing in the direction of the housing opening can be implemented, for example, at least one soldered connection. Moreover, the base body can be connected to the frame element in a variety of ways also, for example, through at least one non-positive fit-type and/or positive fit-type and/or firmly bonded connection, through at least one firmly bonded connection, for example, through a soldered connection and/or a welded connection. In order to promote the wetting of the electrical bushing, for example, of the ceramic base body of the electrical bushing, with solder, at least one metallization of the base body can be provided, for example a metallization that is applied through at least one vapor deposition procedure, for example a sputtering procedure. Said metallization can, for example, include at least one metal selected from the group consisting of gold, titanium and chromium and/or at least one combination and/or at least one multiple layer comprising one or more of said metals.

The frame element is a component of the electrical bushing and can be provided, for example, in a condition, in which the frame element is already connected to the base body. Alternatively, the frame element can just as well be connected to the base body only during the manufacture of the implantable medical device, as illustrated in more detail below, whereby said connecting can be effected before, during or after connecting the frame element to the housing. Accordingly, the frame element, fully or in part, can also be provided as a separate component or even as an integral component of the housing, whereby the electrical bushing in the scope of embodiment 1 may only be generated during the manufacture of the implantable medical device.

As illustrated above, the at least one frame element is provided in order to fix the base body in place in the at least one housing opening of the housing. Said at least one frame element is designed as metallic frame element. The frame element can be designed, for example, as a closed or partly open frame that encloses the at least one optional frame opening. The base body can be attached to the housing through a single frame element or, just as well, through multiple frame elements.

The base body and the frame element can be connected to each other in a variety of ways, which can also be combined as a matter of principle. Moreover, the frame element and the housing can be connected to each other in a variety of ways, which also can be combined with each other. For example, during the manufacture of the implantable medical device, the frame element can first be connected to the base body and subsequently the frame element can be connected to the housing, or vice versa. Overlapping, in terms of timing, and concurrent connection is feasible as well. Accordingly, procedural steps ii. and iii. according to embodiment 29 specified above can be carried out in the order given, in reverse order or overlapping in time or concurrent in time. In said procedural steps, one or more non-positive fit-type and/or positive fit-type and/or firmly bonding connection procedures can be applied, whereby firmly bonding connection procedures are preferred in one embodiment. Accordingly, procedural step ii. and/or iii. can include at least one firmly bonding procedure, for example, a soldering procedure and/or at least one welding procedure.

The frame element can, for example, act as a holding element or be designed, fully or in part, as a holding element. The frame element can, for example, include at least one flange, whereby the flange can, for example, be electrically conductive. The purpose of the flange can be to seal the electrical bushing with respect to a housing of the implantable device. The frame element in one embodiment holds the electrical bushing in the housing. The frame element can, for example, include at least one flange on at least one external side, for example on the circumferential side. Said flange can form a bearing, which, for example, is engaged by the housing of the implantable medical device or parts thereof, for example lids and/or housing shells, engaged in a sealing manner. Accordingly, the frame element having the at least one flange attached can have, for example, a U-, T-, L- or H-shaped cross-section. Integrating at least one flange into the frame element ensures that the electrical bushing is integrated into the implantable device in a safe, impact-resistant and durable manner. In addition, the flange can be designed such that the housing or parts thereof can be connected to it in a positive fit-type manner and/or non-positive fit-type manner, for example through at least one clip-like connection.

As illustrated above, the base body can project, at least in part, into the at least one optional frame opening of the frame element and fill the frame opening at least partly. In the region, which projects into the frame opening, or at least in part of said region, the base body can, for example, have an external shape alike the shape of the frame element, for example to a tolerance of less than 0.5 mm, in one embodiment of less than 0.2 mm, in one embodiment of less than 0.1 mm. Accordingly, the base body can be inserted as a whole or at least a section of it, into the frame element and/or the frame opening, for example in a tight-fit manner, or within the tolerances specified above.

By this or another means, as illustrated above, the frame element and the base body can be provided to act in concert such that the base body can be positioned unambiguously towards the frame element, for example in a self-centering manner. However, alternatively or in addition, one or more positioning aids can be provided on the base body and/or on the frame element, for example mechanically interdigitating positioning aids, for example at least one unambiguous positioning aid on the base body and at least one corresponding unambiguous positioning aid on the frame element, whereby the positioning aids can interdigitate mechanically during an installation. Various other designs are feasible as well.

As described above, the frame element can be provided to have one of various geometries. The base body can, for example, be provided as an annular disc having, for example, a circular, oval or polygonal cross-section. The base body can be placed on the annular disc without projecting into the annular disc or it can be fully accommodated in the annular disc or a section can project into the annular disc.

The frame element, in turn, can be connected to the housing in a variety of ways. For example, the frame element can be placed on the housing proceeding from the internal space or from the external space, for example if at least one spatial dimension of the frame element is larger than the corresponding dimension of the housing opening. Alternatively or in addition, the frame element can just as well be inserted fully or partly into the housing opening and/or project into the housing opening.

As before, in analogy to the design of the frame element and housing, the housing and the frame element can be provided in a manner such that the frame element can be positioned unambiguously towards the housing, for example oriented in a self-centering manner to the at least one housing opening. This can be effected, as before, in that at least one part of the frame element engages the housing opening in a perfect fit or with little tolerance, for example with a tolerance of less than 0.5 mm, in one embodiment less than 0.2 mm, and in one embodiment less than 0.1 mm. Alternatively or in addition, engagement of the frame element by the housing for positioning during an installation shall be feasible as well. Alternatively or in addition, the frame element and/or the housing can just as well include one or more positioning aids which act in concert and, for example, interdigitate in order to ensure the unambiguous positioning described above.

As described in embodiment 13, the frame element can include at least one fastening profile. As a general rule, a fastening profile shall be understood to mean any profile that deviates from a planar resting surface and supports a fastening of the frame element on the housing. Said fastening profile can, for example, be provided such that the frame element partly surrounds the housing or includes at least two contact surfaces to the base body that are arranged at an angle to each other. Accordingly, for example and as illustrated in embodiment 14, an angular or rounded U-shaped profile can be provided, whereby the housing, for example, can be embedded between the arms of the U or project into the space between them. The frame element can be provided, for example, as an annulus-shaped frame element, whereby the U-shaped profile can be provided in a sectional plane perpendicular to the housing and/or perpendicular to the housing opening through the frame element, whereby, for example, the arms of the U each can face outward. Alternatively or in addition, for example, the L-shaped profile can be provided in said sectional plane, whereby, for example, one arm of the L rests on a surface of the housing and the arm perpendicular to said arm can project into the housing opening or can even contact one rim of the housing that faces the housing opening. An analogous design shall also be feasible for the possible H profile and/or the specified T profile.

As illustrated above, the fastening profile can, for example, fully or partly be provided as a flange or include at least one flange. A flange can generally be understood to mean a fastening profile by means of which a tight connection to the housing can be established. The flange can be provided, for example, as a collar that sticks out from the base body and can connect the base body to the housing.

According to another aspect, one embodiment proposes an implantable medical device having the features described above. Features and details that were described in the context of the electrical bushing and/or any of the methods shall also apply in relation to the implantable medical device, and vice versa. Moreover, the implantable medical device can further include, for example, at least one supply lead, which is also called "lead" or "leads" in English and can be set-up to form an electrical connection to the electrical bushing, for example an electrical plug connection. The lead can, for example, include at least one plug element, for example at least one male and/or at least one female plug element, which can form an electrical plug-in connection with the plug connection element of the electrical bushing. This can, for example, be at least one male plug element which can be plugged into the at least one plug connector element, for example at least one plug element according to one or more of the standards, the IS-1 (ISO 5841-3), IS-4, and DF-1 (ISO 11318:1993). Other refinements are feasible as well.

The housing includes the at least one housing opening. The housing opening can basically be of any shape, for example a round, oval or polygonal shape. The housing can, for example, be assembled from multiple housing parts, for example from at least two housing shells, whereby, for example, the housing opening is accommodated in one of the housing parts or in at least two of the housing parts, for example in the form of cut-outs in the housing parts which complement each other to form the housing opening when the housing parts are joined. The housing can, for example, be manufactured fully or in part from a metallic material, for example, from titanium or a titanium alloy. Alternatively or in addition, any other materials can be used just as well, for example one or more of the materials specified above with regard to the frame element.

At least one electrical connection between at least one internal space of the housing and at least one external space is established through the electrical bushing. The housing opening can be closed, for example, and as specified above, in a hermetically sealed manner by the electrical bushing.

Another aspect of one embodiment proposes a method for the manufacture of an electrical bushing according to one embodiment and a method for the manufacture of an implantable medical device, as illustrated above. Features and details that are described in the context of the electrical bushing and/or in the context of the implantable medical device shall also apply accordingly in relation to the methods according to the embodiments, and vice versa. With regard to the steps of the method, reference shall be made to the description of the embodiments provided above. The methods can be carried out in the order of the procedural steps illustrated or in any other order. Moreover, procedural steps can also be carried out concurrently or overlapping in time. Moreover, the methods can include one or more additional procedural steps that are not illustrated.

The manufacture of the base body and the insertion of the at least one conducting element into the base body can proceed in various partial steps of procedural step a. Alternatively, said partial steps can be combined fully or in part such that the manufacturing of the base body proceeds in such a manner that the at least one conducting element is already inserted into the base body after the manufacture is completed. This means, for example, as illustrated above, that, in a ceramic manufacturing procedure for the base body and for the at least one conducting element, separate green compacts can be produced initially, which are later connected to form a common green compact, which is then sintered, for example. Alternatively, at least one common green compact can be manufactured for the base body and the at least one conducting element. Accordingly, inserting the conducting element into the base body is generally to be understood to mean a method, in which at least one conducting element is already inserted into the base body after completion of the method. The at least one conducting element can, for example, be embedded, fully or in part, into the base body and/or connected in a firmly bonded manner to the base body. However, other designs are also feasible as a matter of principle. The connecting of the base body to the at least one frame element in procedural step c. can proceed in a variety of ways that have already been illustrated above.

The proposed electrical bushing, the implantable medical device, and the methods provide a large number of advantages as compared to known devices and methods of the specified type. Accordingly, a cost-efficient manufacturing method can be implemented which features high process reliability and low waste production at the same time. For example, according to one embodiment, the number of boundary surfaces can be reduced which allows the potential of errors to be generally reduced. The boundary surfaces being reduced reduces, for example, the ingress of moisture or body fluid. Simultaneously, the use of ceramic materials allows high mechanical stability and strong sealing against moisture, for example, body fluid, to be implemented. Accordingly, the proposed bushings have a long service life. Simultaneously, unlike in conventional methods, a plurality of procedural steps can be combined and, optionally, automated in the scope of customary ceramic manufacturing procedures.

Figure 2:
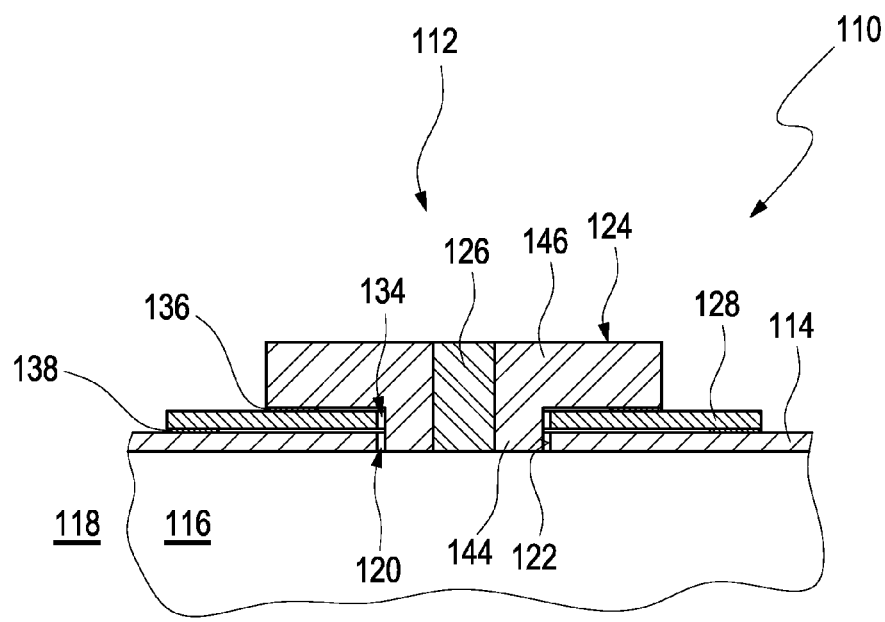

FIGS. 1 and 2 illustrate sectional views of details of various exemplary embodiments of implantable medical devices 110 having at least one electrical bushing 112 and at least one housing 114. The housing 114 fully or partly surrounds at least one internal space of the implantable medical device 110, which is symbolically denoted through reference number 116 in the figures, and in one embodiment closes said internal space 116 in hermetically sealed manner with respect to an external space 118 that is situated outside the housing 114. For example one or more functional elements of the implantable medical device 110 can be arranged in said internal space 116. With regard to the basic structure of the implantable medical device 110, reference shall be made, for example, to the references specified above, for example U.S. Pat. No. 7,260,434 B1. The implantable medical device 110 can include one or more electrical bushings 112, whereby multiple electrical bushings 112 can just as well be combined into a bushing block or connector block and/or can be integrated fully or partly in a so-called head part (header) of the implantable medical device 110.

The housing 114 includes at least one housing opening 120 that has at least one rim 122 of the housing 114 facing the housing opening 120. Said housing opening 120 is closed through the at least one electrical bushing 112 at least in part or, in one embodiment, fully, and in one embodiment, in a hermetically sealed manner.

The electrical bushing 112 includes one base body 124 each in the exemplary embodiments illustrated in FIGS. 1 and 2. However, refinements having multiple base bodies 124 are feasible just as well. The base body 124 can, for example and as specified above, be manufactured fully or in part from at least one ceramic material, for example from one or more of the ceramic materials specified above. The base body 124 has electrically insulating properties.

Moreover, the electrical bushing 112 includes at least one electrical conducting element 126. In one embodiment, said conducting element 126 is embedded in the base body 124 in a firmly bonded manner, for example in a through-opening in the base body 124. One conducting element 126 is provided in each of the exemplary embodiments according to FIGS. 1 and 2. However, as is illustrated in the following exemplary embodiments, electrical bushings 112 having a larger number of conducting elements 126 are feasible as well. Moreover, the conducting element 126 can end flush with the base body 124 on the side of the base body 124 facing the internal space 116 and/or on the side of the base body 124 facing the external space 118, as is illustrated in exemplary manner in FIGS. 1 and 2, or it can project into the internal space 116 and/or the external space 118. Other refinements are feasible as well, for example refinements, in which the conducting element 126 does not extend fully from the internal space 116 to the external space, but rather extends through only part of the base body 124 and, for example, acts in concert with other conductive elements. As illustrated above, the conducting element 126 is made from a cermet either fully or in part. For possible compositions of the cermet, reference shall be made to the description above. In one embodiment, the cermet and the base body 124 can include one or more of the same ceramic component.

Moreover, the electrical bushings 112 according to the exemplary embodiments illustrated in FIGS. 1 and 2 each include at least one frame element 128 that is provided as metallic frame element and set up to fix the base body 124 in place in the housing opening 120. As illustrated above, the term, fixation "in the housing opening 120," according to the scope of one embodiment does not necessarily mean that the base body 124 needs to extend into the housing opening 120, but rather it only means that the base body 124 is fixed in place with respect to the housing opening 120 and, for example, closes the housing opening 120 fully or in part.

In the exemplary embodiment according to FIG. 1, the base body 124 is provided to be essentially disc-shaped having a surface 130 facing the internal space 116 and a surface 132 facing the external space 118. Said surfaces 130, 132 can be arranged, for example, to be parallel to each other. The disc-shaped base body 124 can, for example, have a round, an oval or a polygonal, in one embodiment a rectangular or square, cross-section in a sectional plane perpendicular to the drawing plane in FIG. 1. However, other cross-sections are also feasible as a general rule. The disc of the base body 124 can be arranged, for example, fully in said external space 118, as illustrated in FIG. 1, or just as well in the internal space 116. Moreover, a refinement is conceivable just as well, in which the disc of the base body 124 is arranged in the housing opening 120.

In the exemplary embodiment illustrated in FIG. 1 or other exemplary embodiments, the frame element 128 can include a frame opening 134, which can have any cross-section as a general rule, but in one embodiment has a round, an oval or a polygonal, for example a square or generally rectangular, cross-section. The dimensions of said frame opening 134, for example an equivalent diameter of said frame opening 134, can be provided to be larger than, equal to or smaller than the corresponding dimensions of the housing opening 120. In the exemplary embodiment illustrated in FIG. 1, the frame element 128 is provided as an annular disc, for example as a circular annular disc, in one embodiment as a washer. The frame element 128 can generally be made from a metallic material, for example from at least one of the metallic materials specified above. The use of titanium is preferred in one embodiment. Regarding the external dimensions, the frame element 128 can protrude beyond the external dimensions of the base body 124 as illustrated in FIG. 1. Alternatively, the frame element 128 can end flush with the base body 124 or have smaller dimensions than the base body 124.

The base body 124 is connected to the frame element 128 through at least one connection, in one embodiment at least one hermetically sealed connection. This is illustrated symbolically in FIG. 1 through a firmly bonded connection 136, which can extend, for example, annular-shaped around the frame opening 134 and/or the housing opening 120. Said firmly bonded connection 136 can, for example, be a soldered connection. In order to establish said connection, the disc-shaped base body 124 can be placed on and be soldered and/or welded to the disc-shaped frame element 128. Subsequently, concurrently or earlier, the frame element 128 can be connected to the housing 114 through at least one connection. This is again illustrated symbolically in FIG. 1 through a firmly bonded connection 138 between the frame element 128 and the housing 114. As before, this connection is in one embodiment hermetically sealed. This connection can, for example, again extend in annular shape around the frame opening 134 and/or the housing opening 120.

In order to improve a sealing of the firmly bonded connection 136 between the frame element 128 and the base body 124, in one embodiment a ceramic base body, the base body 124 can generally include at least one metallization, not illustrated in the figures, on at least one side facing the firmly bonded connection 136. A metallization of said type can, for example, be a metallization made of one or more of the materials specified above. A metallization of said type can be applied to the base body 124, for example, through a physical vapor deposition method, for example through a sputtering procedure, for example by metallizing just one surface of the base body 124 which later is in contact with the firmly bonded connection 136. Through this means, for example a wetting of said metallized surface with a solder can be improved.

Moreover, it is evident from the exemplary embodiment according to FIG. 1, that the conducting element 126 can be connected to and/or supplemented through further conductive elements, as illustrated above. Accordingly, for example as an option, one or more contact elements 140, 142 are provided in the exemplary embodiment illustrated in FIG. 1 on the surface 130 facing the internal space 116 and/or the surface 132 facing the external space 118, which contact elements can, for example, be provided in the form of one or more contact surfaces or similar contact elements and which, for example, shall enable or facilitate electrical contacting of the conducting element 126. More complex refinements than the disc-shaped refinements of the contact elements 140, 142 illustrated in FIG. 1 shall be feasible just as well, for example complex refinements in the form of plug pins, plug sockets, contact springs, contact pins, strip conductor structures or other designs. The contact elements 140, 142 can be provided, for example, as the same part as the conducting element 126 and/or be connected to same in a conductive manner, for example through an electrically conductive firmly bonded connection and/or an electrically conductive non-positive fit-type and/or positive fit-type connection.

With regard to the design of the exemplary embodiment according to FIG. 2, reference shall largely be made to the description of the exemplary embodiment according to FIG. 1 provided above. The exemplary embodiment according to FIG. 2 differs from the exemplary embodiment according to FIG. 1 essentially through the design of the base body 124. In contrast to the disc-shaped design according to FIG. 1, the exemplary embodiment according to FIG. 2 illustrates that the base body 124 may just as well be more complex in shape. In said exemplary embodiment, the base body 124 can, for example, include at least one first section 144 that projects into the frame opening 134 and/or into the housing opening 120, and at least one second section 146 that is arranged external to the frame opening 134 and/or external to the housing opening 120. For example, both the first section 144 and the second section 146 can each be cylindrical in shape, for example with a circular, an oval or a polygonal diameter. The first section 144 can, for example, have smaller dimensions than the second section 146, for example a smaller diameter or smaller equivalent diameter. The external dimensions of the first section 144 can, for example, be adapted to the internal dimensions of the housing opening 120 and/or of the frame opening 134 or can be dimensioned to be smaller. In one embodiment, the base body and/or the frame element 128 can be provided such that the base body can be unambiguously positioned with respect to the frame element, in one embodiment can be centered. This is the case in exemplary manner in the exemplary embodiment according to FIG. 2, since, for example, the dimensions of the first section 144 can be adapted to the frame opening 134 such that, for example, the base body 124 can self-center with respect to the frame element 128. Alternatively or in addition, appropriate dimensioning of the frame element 128 and/or of the first section 144 of the base body 124 can enable unambiguous positioning with respect to the housing opening 120, for example again through self-centering.

FIGS. 3 to 8 illustrate various further exemplary embodiments of electrical bushings 112. These can be connected to a housing 114 of an implantable medical device 110, for example in analogous ways to the exemplary embodiments illustrated in FIGS. 1 and 2. Accordingly, regarding the elements illustrated and their optional design, reference shall largely be made to the description of FIGS. 1 and 2 provided above. As before, optional firmly bonded connections 136 between the base body 124 and the frame element 128 are provided in an exemplary manner. However, other designs are also feasible.

Figure 3:
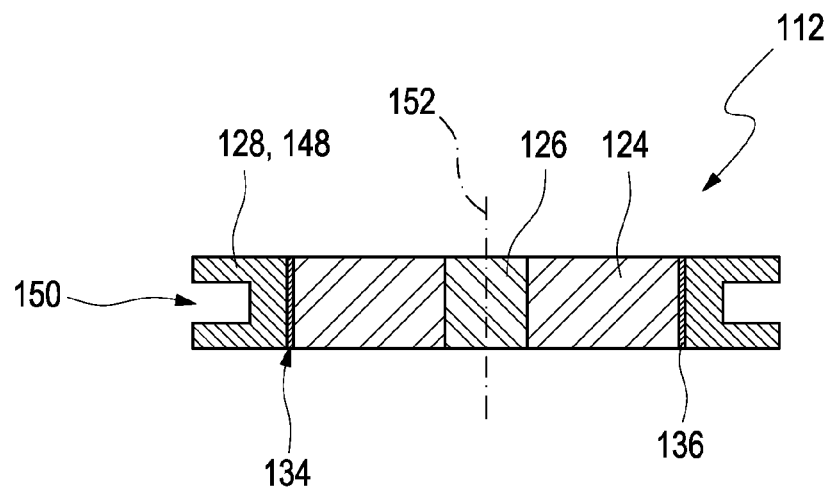
FIGS. 3 to 8 illustrate electrical bushings according to further exemplary embodiments for use in an implantable medical device.

FIG. 3 illustrates an exemplary embodiment, in which the frame element 128 surrounds the base body 124 in a ring-shaped manner such that the base body 124 closes a frame opening 134 of the frame element 128 fully or partly and, in one embodiment, hermetically. Likewise, the base body 124 and/or a connection between the base body 124 and the frame element 128 in one embodiment hermetically closes the frame opening 134 in the remaining exemplary embodiments also. The base body 124 can, for example, again be connected to the frame element 128 in a firmly bonded manner. Said firmly bonded connection can be established during manufacture or subsequently, for example again through a soldered connection and/or a welded connection. The firmly bonded connection is not illustrated in the following figures.

The electrical bushing 112 according to the exemplary embodiment in FIG. 3 can, for example, be provided as a disc-shaped electrical bushing and can, for example, be introduced fully or at least partly into a housing opening 120 of a housing 114 (not illustrated). Accordingly, the frame element 128 can be connected, for example, to the rim 122 of the housing 114 illustrated in FIGS. 1 and 2 and/or to a side of the housing 114 facing the external space 118 and/or to a side of the housing 114 facing the internal space 116. The frame element 128 is provided as a flange 148 and includes a fastening profile 150 in the exemplary embodiment illustrated in FIG. 3. Said fastening profile 150 is provided, in exemplary manner, to be U-shaped in the exemplary embodiment illustrated, whereby the arms of the U point away from an axis 152 of the electrical bushing 112 towards the outside. Said arms can, for example, surround or clasp the rim 122 of the housing 114. One or both of the arms of the fastening profile 150 can then, for example, be connected to the housing 114.

Figure 4:
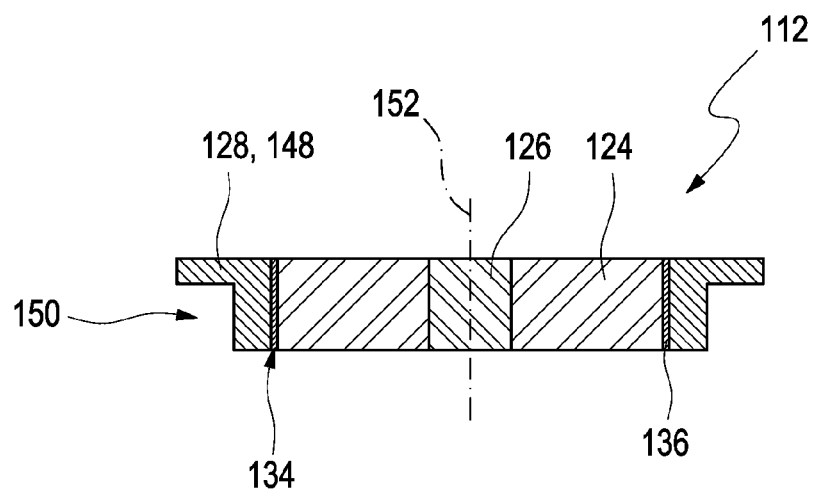

FIG. 4 illustrates an exemplary embodiment of the electrical bushing 112 which is essentially the same as the exemplary embodiment according to FIG. 3. However, the fastening profile 150 in said exemplary embodiment is provided to be L-shaped, that is, in the shape of an inverted or lying down L. Said L can be introduced into the housing opening 120, for example, by proceeding from the internal space 116 or from the external space 118. The L of the fastening profile 150 can be appropriately dimensioned, for example, such that the electrical bushing 112 is self-centering in the housing opening 120 or can generally be positioned unambiguously.

Figure 5:
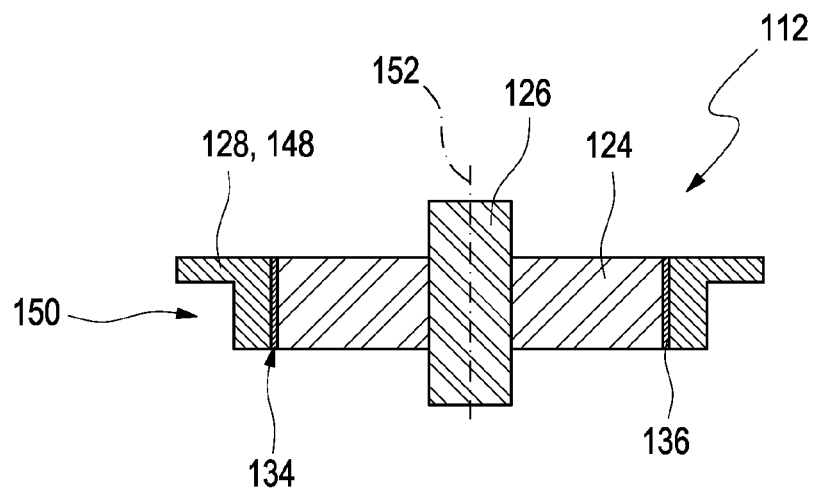

FIG. 5 illustrates an exemplary embodiment of the electrical bushing 112 which can essentially be the same as the exemplary embodiment according to FIG. 4. As has been discussed above based on FIG. 1, the exemplary embodiment according to FIG. 5 illustrates though that the at least one conducting element 126 in this or other exemplary embodiments does not necessarily have to end flush with the base body 124, but rather can project into the internal space 116 and/or the external space 118. More complex designs are also feasible as a general rule.

Figure 6:
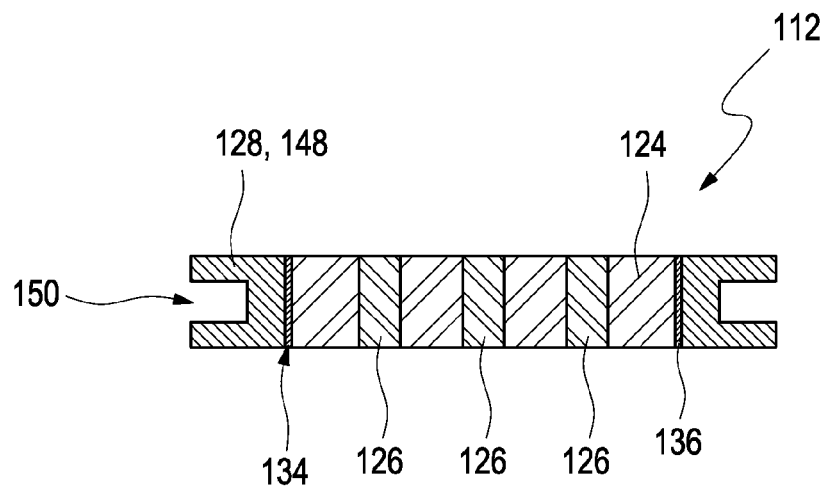

FIG. 6 illustrates an exemplary embodiment of the electrical bushing 112 which is essentially the same, in exemplary manner, as the exemplary embodiment according to FIG. 3. As a general rule, other designs of the frame element 128 shall be feasible as well, for example designs according to the other exemplary embodiments. However, the exemplary embodiment according to FIG. 6 illustrates that multiple conducting elements 126 can be provided in the base body 124.

Figure 7:
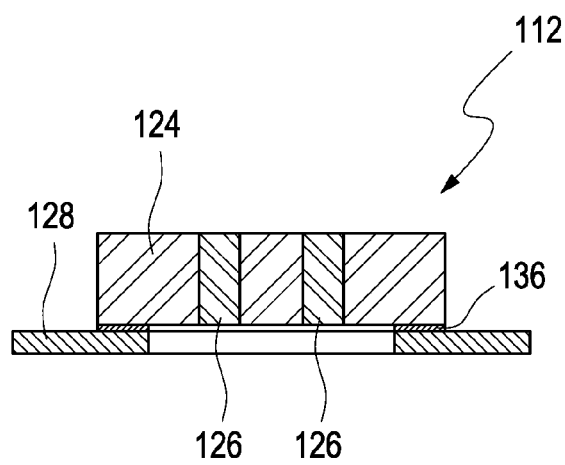

FIG. 7 illustrates, in exemplary manner, an exemplary embodiment of the electrical bushing 112 that is essentially the same as the exemplary embodiment according to FIG. 1, but has multiple conducting elements 126 in analogy to the exemplary embodiment according to FIG. 6.

Figure 8:
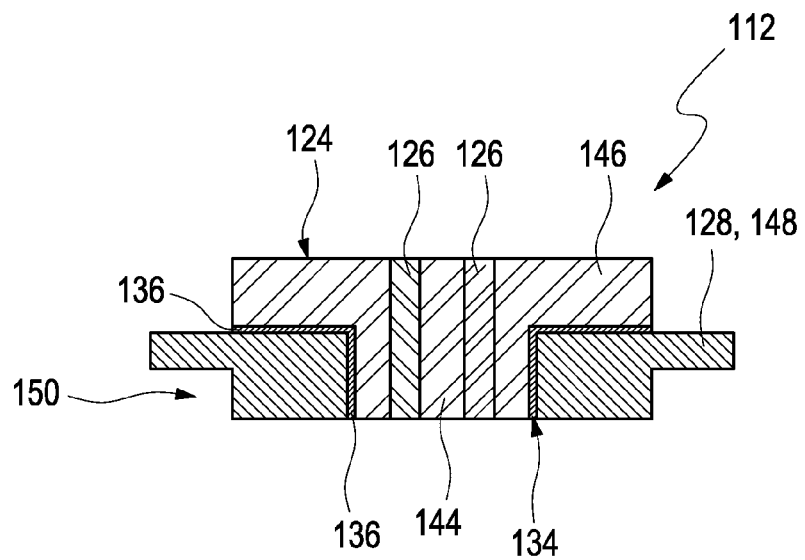

FIG. 8 illustrates an exemplary embodiment that illustrates that, for example, the exemplary embodiments according to FIGS. 2, 4, and 7 can be combined as well. Accordingly, said exemplary embodiment provides multiple conducting elements 126 in analogy, for example, to FIGS. 6 and 7. Obviously, just a single conducting element 126 can be provided just as well. Moreover, the base body 124 is optionally provided such that it includes a first section 144 which can project into a frame opening 134 and, optionally, beyond said frame opening into a housing opening 120 (not illustrated). In contrast, at least one second section 146 can be placed on a side of the frame element 128 facing the external space 118 and/or on a side of the frame element 128 facing the internal space 116, and/or can be dimensioned to be larger than the frame opening 134. Moreover, said exemplary embodiment illustrates that, again, the frame element 128 can be equipped with a fastening profile 150, in exemplary manner this is a fastening profile 150 according to the exemplary embodiments in FIGS. 4 and 5. However, other designs of the fastening profile 150 shall be feasible just as well, for example designs according to FIGS. 3 and 6 or a simple disc-shaped design of the frame element 128, for example according to the exemplary embodiments in FIGS. 2 and 7.

Exemplary Embodiment of Ceramic Compositions:

An exemplary embodiment of a ceramic material for the base body 124 and the at least one electrical conducting element 126 that can be used is illustrated in the following. However, embodiments shall not be limited to said exemplary embodiment.

In a first step, a cermet mass was produced from platinum (Pt) and aluminum oxide ($Al_2O_3$) containing 10% zirconium dioxide ($ZrO_2$). The following starting materials were used for this purpose:

40 vol. % Pt powder with a mean grain size of 10 µm, and
60 vol. % $Al_2O_3/ZrO_2$ powder with a relative $ZrO_2$ content of 10% and a mean grain size of 1 µm.

The two components were mixed, water and a binding agent were added, and the sample was homogenized through a kneading process.

Analogous to the first step, a ceramic mass was produced in a second step from a powder with an $Al_2O_3$ content of 90% and a $ZrO_2$ content of 10%. The mean grain size was approx. 1 µm. As before, water and a binding agent were added to the ceramic powder and the sample was homogenized.

In a third step, the ceramic mass made of aluminum oxide with a 10% zirconium dioxide content produced in step 2 was converted to a shape of a base body 124. A cermet body, which was made from the cermet mass produced in step 1 and contained a mixture of platinum powder and aluminum oxide with a zirconium dioxide content of 10%, was introduced as green compact into an opening in the green compact of the base body 124. Subsequently, the ceramic mass was compacted in the mold. Then the cermet and the ceramic component were subjected to debinding at 500° C. and the sintering was finished at 1650° C.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. An electrical bushing for use in a housing of an implantable medical device;
whereby the electrical bushing comprises at least one electrically insulating base body and at least one electrical conducting element;
whereby the conducting element establishes, through the base body, at least one electrically conductive connection between an internal space of the housing and an external space;
whereby the conducting element is hermetically sealed with respect to the base body, at least in part;
whereby the at least one conducting element comprises at least one cermet; and
characterized in that the cermet of the conducting element and the base body include one or more of a same ceramic compound and in that the electrical bushing hermetically seals the housing of the implantable medical device such that the housing comprises a helium leak rate of less than $1 \times 10^{-7}$ atm*$cm^3$/sec.

2. The electrical bushing according to claim 1, characterized in that the cermet of electrical bushing comprises a metal component, selected from a group consisting of: platinum, a platinum alloy, iridium, niobium, molybdenum, titanium, a titanium alloy, cobalt, zirconium, chromium, tantalum, a tantalum alloy, tungsten, a tungsten alloy, and in that the cermet of electrical bushing comprises a ceramic component selected from a group consisting of: aluminum oxide, $Al_2O_3$, zirconium oxide, $ZrO_2$, magnesium oxide, MgO, ZTA, ATZ, Y-TZP, aluminum nitride, aluminum titanate, a piezoceramic material, and a lead-free piezoceramic material.

3. The electrical bushing according to claim 2, characterized in that the base body comprises a ceramic component selected from a group consisting of: aluminum oxide, $Al_2O_3$, zirconium oxide, $ZrO_2$, magnesium oxide, MgO, ZTA, ATZ, Y-TZP, aluminum nitride, aluminum titanate, a piezoceramic material, and a lead-free piezoceramic material.

4. The electrical bushing according to claim 1, characterized in that the cermet of electrical bushing comprises a platinum metal component and an aluminum oxide ceramic component, and in that the base body comprises an aluminum oxide ceramic component.

5. The electrical bushing according to claim 1, characterized in that the cermet of electrical bushing comprises a platinum metal component and an $Al_2O_3/ZrO_2$ ceramic component, and in that the base body comprises an $Al_2O_3/ZrO_2$ ceramic component.

6. The electrical bushing according to claim 1, characterized in that the electrical bushing comprises at least one metallic frame element, whereby the frame element fixes the base body in at least one housing opening of the housing.

7. The electrical bushing according to claim 6, characterized in that the frame element comprises at least one frame opening, whereby the frame element is connected to the base body in a manner such that the base body and the conducting element close the frame opening in a hermetically sealed manner.

8. The electrical bushing according to claim 7, characterized in that the base body projects into the frame opening, at least in part, and fills the frame opening, at least in part.

9. The electrical bushing according to claim 8, characterized in that the frame element is connected to the base body through at least one firmly bonded connection, through at least one soldered connection and/or at least one welded connection.

10. The electrical bushing according to claim 9, characterized in that the base body comprises at least one metallization at least in a region that faces the firmly bonded connection.

11. An implantable medical device comprising:
at least one housing having at least one housing opening, at least one internal space; and an electrical bushing comprising at least one electrically insulating base body of a ceramic compound and at least one electrical conducting element, the conducting element comprising at least one cermet and, at least in part, is hermetically sealed with respect to the base body;

wherein the electrical bushing is connected to the housing and over the at least one housing opening such that the implantable medical device is hermetically sealed having a helium leak rate of less than $1\times10^{-7}$ atm*cm$^3$/sec;

wherein the electrical bushing establishes at least one electrical connection between the at least one internal space of the housing and at least one external space; and wherein the cermet of the conducting element and the base body include the same ceramic compound.

12. The implantable medical device according to claim 11, characterized in that the cermet of electrical bushing comprises a platinum metal component and an aluminum oxide ceramic component, and in that the base body comprises an aluminum oxide ceramic component.

13. The implantable medical device according to claim 11, wherein the cermet of electrical bushing comprises a platinum metal component and an $Al_2O_3/ZrO_2$ ceramic component, and wherein the base body comprises an $Al_2O_3/ZrO_2$ ceramic component.

14. The implantable medical device according to claim 11, wherein a frame element is connected between the electrical bushing and the housing in a firmly bonded manner through at least one soldered connection and/or one welded connection.

* * * * *